US010030068B2

(12) United States Patent
Olichon et al.

(10) Patent No.: US 10,030,068 B2
(45) Date of Patent: *Jul. 24, 2018

(54) SYNTHETIC SINGLE DOMAIN ANTIBODY

(71) Applicants: INSERM (Institut National de la Sante et de la Recherche Medicale), Paris (FR); Institut Curie, Paris (FR); Universite Paul Sabatier Toulouse III, Toulouse (FR); Centre National de la Recherche Scientifique (CNRS), Paris (FR)

(72) Inventors: Aurelien Olichon, Toulouse (FR); Sandrine Moutel, Paris (FR); Franck Perez, Paris (FR)

(73) Assignees: INSERM (Institut National de la Sante et de la Recherche Medicale), Paris (FR); Institut Curie, Paris (FR); Universite Paul Sabatier Toulouse III, Toulouse (FR); Centre National de la Recherche Scientifique (CNRS), Paris (FR)

(*) Notice: Subject to any disclaimer, the term of this patent is extended or adjusted under 35 U.S.C. 154(b) by 0 days.

This patent is subject to a terminal disclaimer.

(21) Appl. No.: 15/638,509

(22) Filed: Jun. 30, 2017

(65) Prior Publication Data

US 2018/0030117 A1     Feb. 1, 2018

Related U.S. Application Data

(63) Continuation of application No. 15/030,541, filed as application No. PCT/EP2014/073713 on Nov. 4, 2014.

(30) Foreign Application Priority Data

Nov. 4, 2013   (EP) ..................... 13191444

(51) Int. Cl.
*C40B 40/10*    (2006.01)
*C07K 16/00*    (2006.01)
(Continued)

(52) U.S. Cl.
CPC ............ *C07K 16/005* (2013.01); *C07K 16/32* (2013.01); *C07K 16/40* (2013.01); *C07K 16/44* (2013.01);
(Continued)

(58) Field of Classification Search
None
See application file for complete search history.

(56) References Cited

U.S. PATENT DOCUMENTS

2012/0301469 A1* 11/2012 Depla ................ C07K 16/1027
424/135.1

FOREIGN PATENT DOCUMENTS

EP    1433793 A1    6/2004
WO    0190190 A2   11/2001
(Continued)

OTHER PUBLICATIONS

Muyldermans, "Single Domain Camel Antibodies: Current Status", Reviews in Molecular Biotechnology, Jun. 1, 2001, vol. 74, No. 4, p. 277-302.

(Continued)

*Primary Examiner* — Christian C Boesen
(74) *Attorney, Agent, or Firm* — W&C IP

(57) ABSTRACT

The invention relates to the identification of a highly stable single domain antibody scaffold (hs2d Ab) and its use in generating synthetic single domain antibody library (hs2d Ab-L1). The invention also relates to antigen-binding proteins comprising said stable single domain antibody scaffold and their uses, in particular as therapeutics.

4 Claims, 5 Drawing Sheets

Figure 3A:
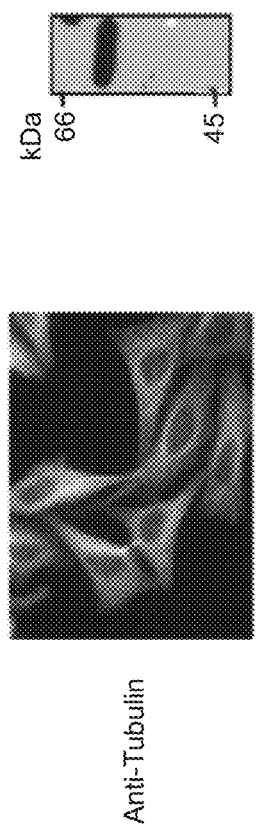

(51) Int. Cl.
*C07K 16/40* (2006.01)
*C07K 16/44* (2006.01)
*C07K 16/32* (2006.01)

(52) U.S. Cl.
CPC ...... *C07K 2317/22* (2013.01); *C07K 2317/24* (2013.01); *C07K 2317/565* (2013.01); *C07K 2317/569* (2013.01); *C07K 2317/76* (2013.01); *C07K 2317/80* (2013.01); *C07K 2317/92* (2013.01); *C40B 40/10* (2013.01)

(56) References Cited

FOREIGN PATENT DOCUMENTS

| WO | 2010001251 A1 | 1/2010 |
| WO | 2011080350 A1 | 7/2011 |

OTHER PUBLICATIONS

Vincke et al., "General Strategy to Humanize a Camelid Single-Domain Antibody and Identification of a Universal Humanized Nanobody Scaffold", Journal of Biological Chemistry, Jan. 30, 2009, vol. 284, No. 5, p. 3273-3284.

Almagro et al., "Humanization of Antibodies", Frontiers in Bioscience, Jan. 1, 2008, vol. 13, p. 1619-1633.

Tanha et al., "Selection by Phage Display of Llama Conventional VH Fragments with Heavy Chain Antibody VHH Properties", Journal of Immunological Methods, May 1, 2002, vol. 263, No. 1-2, p. 97-109.

\* cited by examiner

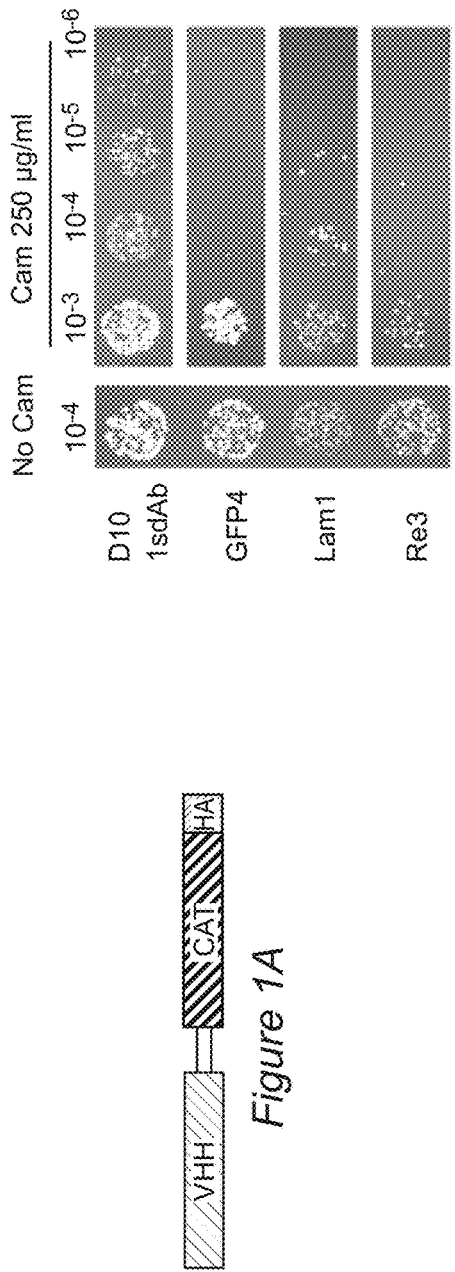

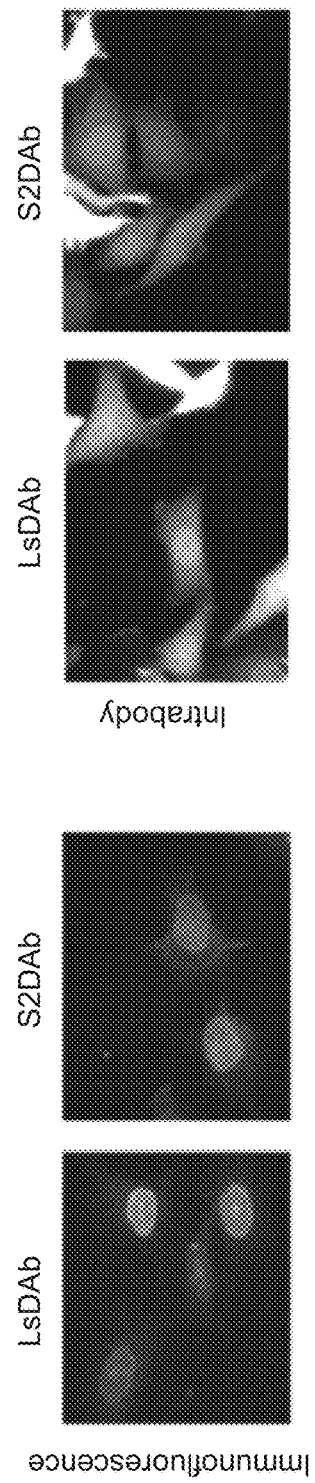

SEQUENCE LISTING

<160> NUMBER OF SEQ ID NOS: 25

<210> SEQ ID NO 1
<211> LENGTH: 25
<212> TYPE: PRT
<213> ORGANISM: Artificial Sequence
<220> FEATURE:
<223> OTHER INFORMATION: synthetic single domain

<400> SEQUENCE: 1

Val Gln Leu Gln Ala Ser Gly Gly Gly Phe Val Gln Pro Gly Gly Ser
1               5                   10                  15

Leu Arg Leu Ser Cys Ala Ala Ser Gly
            20                  25

<210> SEQ ID NO 2
<211> LENGTH: 19
<212> TYPE: PRT
<213> ORGANISM: Artificial Sequence
<220> FEATURE:
<223> OTHER INFORMATION: synthetic single domain

<400> SEQUENCE: 2

Met Gly Trp Phe Arg Gln Ala Pro Gly Lys Glu Arg Glu Phe Val Ser
1               5                   10                  15

Ala Ile Ser

<210> SEQ ID NO 3
<211> LENGTH: 39
<212> TYPE: PRT
<213> ORGANISM: Artificial Sequence
<220> FEATURE:
<223> OTHER INFORMATION: synthetic single domain

<400> SEQUENCE: 3

Tyr Tyr Ala Asp Ser Val Lys Gly Arg Phe Thr Ile Ser Arg Asp Asn
1               5                   10                  15

Ser Lys Asn Thr Val Tyr Leu Gln Met Asn Ser Leu Arg Ala Glu Asp
            20                  25                  30

Thr Ala Thr Tyr Tyr Cys Ala
        35

<210> SEQ ID NO 4
<211> LENGTH: 12
<212> TYPE: PRT
<213> ORGANISM: Artificial Sequence
<220> FEATURE:
<223> OTHER INFORMATION: synthetic single domain

<400> SEQUENCE: 4

Tyr Trp Gly Gln Gly Thr Gln Val Thr Val Ser Ser
1               5                   10

<210> SEQ ID NO 5
<211> LENGTH: 84
<212> TYPE: DNA
<213> ORGANISM: Artificial Sequence
<220> FEATURE:
<223> OTHER INFORMATION: synthetic single domain

<400> SEQUENCE: 5
atggcggaag tgcagctgca ggcgagcggc ggcggctttg tgcagccggg cggcagcctg      60
cgtctgagct gcgcggcgag cggc                                            84

<210> SEQ ID NO 6
<211> LENGTH: 57
<212> TYPE: DNA
<213> ORGANISM: Artificial Sequence
<220> FEATURE:
<223> OTHER INFORMATION: synthetic single domain

<400> SEQUENCE: 6
atgggctggt tcgtcaggc gccgggcaaa gaacgtgaat tgtgagcgc gattagc           57

<210> SEQ ID NO 7
<211> LENGTH: 117
<212> TYPE: DNA
<213> ORGANISM: Artificial Sequence
<220> FEATURE:
<223> OTHER INFORMATION: synthetic single domain

<400> SEQUENCE: 7
tattatgcgg atagcgtgaa aggccgtttt accattagcc gtgataacag caaaaacacc      60
gtgtatctgc agatgaacag cctgcgtgcg aagataccg ctacgtatta ttgcgcg         117

<210> SEQ ID NO 8
<211> LENGTH: 45
<212> TYPE: DNA
<213> ORGANISM: Artificial Sequence
<220> FEATURE:
<223> OTHER INFORMATION: synthetic single domain

<400> SEQUENCE: 8
tattggggcc agggcaccca ggtgaccgtg agcagcgcgg ccgca                      45

<210> SEQ ID NO 9
<211> LENGTH: 119
<212> TYPE: PRT
<213> ORGANISM: Lama glama

<400> SEQUENCE: 9

Val Gln Leu Gln Glu Ser Gly Gly Gly Phe Val Gln Ala Gly Gly Ser
1               5                   10                  15

Leu Arg Leu Ser Cys Ala Ala Ser Gly Phe Thr Phe Ser Ser Tyr Ala
            20                  25                  30

Met Gly Trp Phe Arg Gln Ala Pro Gly Lys Glu Arg Glu Phe Val Ala
        35                  40                  45

Ala Ile Ser Asp Ser Ser Gly Asn His Ala Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Thr Tyr Tyr Cys
                85                  90                  95

Ala Arg Ser Asp Ala Ala Gly Asn Pro Ser Gly Tyr Trp Gly Gln Gly
            100                 105                 110

Thr Gln Val Thr Val Ser Ser
        115

<210> SEQ ID NO 10
<211> LENGTH: 119
<212> TYPE: PRT
<213> ORGANISM: Artificial Sequence
<220> FEATURE:
<223> OTHER INFORMATION: synthetic single domain

<400> SEQUENCE: 10

Val Gln Leu Gln Ala Ser Gly Gly Gly Phe Val Gln Pro Gly Gly Ser
1               5                   10                  15

Leu Arg Leu Ser Cys Ala Ala Ser Gly Phe Thr Phe Ser Ser Tyr Ala
            20                  25                  30

Met Gly Trp Phe Arg Gln Ala Pro Gly Lys Glu Arg Glu Phe Val Ser
        35                  40                  45

Ala Ile Ser Asp Ser Ser Gly Asn His Ala Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Thr Tyr Tyr Cys
                85                  90                  95

Ala Arg Ser Asp Ala Ala Gly Asn Pro Ser Gly Tyr Trp Gly Gln Gly
            100                 105                 110

Thr Gln Val Thr Val Ser Ser
        115

<210> SEQ ID NO 11
<211> LENGTH: 78
<212> TYPE: DNA
<213> ORGANISM: Artificial Sequence
<220> FEATURE:
<223> OTHER INFORMATION: Synthetic oligonucleotide Primer

<400> SEQUENCE: 11
cccaccaaac ccaaaaaaag agatcctaga actagctatg gccggacggg ccatggcgga      60
agtgcagctg caggcttc                                                   78

<210> SEQ ID NO 12
<211> LENGTH: 74
<212> TYPE: DNA
<213> ORGANISM: Artificial Sequence
<220> FEATURE:
<223> OTHER INFORMATION: synthetic single domain

<400> SEQUENCE: 12
accgggcctc tagacactag ctactcgagg ggccccagtg gccctatcta tgcggccgcg      60
ctactcacag ttac                                                       74

<210> SEQ ID NO 13
<211> LENGTH: 72
<212> TYPE: DNA
<213> ORGANISM: Artificial Sequence
<220> FEATURE:
<223> OTHER INFORMATION: synthetic single domain

<400> SEQUENCE: 13
ccttgattct agaaataatt tgtttaact ttaagaagga gatataccat gctgatgtcc       60
agctgcaggc gt                                                          72

<210> SEQ ID NO 14
<211> LENGTH: 46
<212> TYPE: DNA
<213> ORGANISM: Artificial Sequence
<220> FEATURE:
<223> OTHER INFORMATION: Synthetic oligonucleotide primer

<400> SEQUENCE: 14
ccaccgctac cgccgctgcg gccgcgtgag gagacggtga cctggg                     46

<210> SEQ ID NO 15
<211> LENGTH: 50
<212> TYPE: DNA
<213> ORGANISM: Artificial Sequence
<220> FEATURE:
<223> OTHER INFORMATION: Synthetic oligonucleotide primer

<400> SEQUENCE: 15
gcggccgcag cggcggtagc ggtggcgaga aaaaaatcac tggatatacc                 50

<210> SEQ ID NO 16
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 16
gcccatcgtg aaaacggggg cg                                               22

<210> SEQ ID NO 17
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 17 cgccccccgtt ttcacgatgg gc                                              22

<210> SEQ ID NO 18
<211> LENGTH: 66
<212> TYPE: DNA
<213> ORGANISM: Artificial Sequence
<220> FEATURE:
<223> OTHER INFORMATION: Synthetic oligonucleotide primer

<400> SEQUENCE: 18
agaataggta ccagcgtaat ctgggacatc ataagggtag ccacccgccc cgccctgcac      60
tcatcg                                                                 66

<210> SEQ ID NO 19
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 19
aacatgccat cactcagatt ctcg                                             24

<210> SEQ ID NO 20

-continued

```
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 20
gttagtccat attcagtatt atcg                                           24

<210> SEQ ID NO 21
<211> LENGTH: 28
<212> TYPE: PRT
<213> ORGANISM: Lama glama

<400> SEQUENCE: 21

Met Ala Glu Val Gln Leu Gln Glu Ser Gly Gly Gly Phe Val Gln Ala
1               5                   10                  15

Gly Gly Ser Leu Arg Leu Ser Cys Ala Ala Ser Gly
            20                  25

<210> SEQ ID NO 22
<211> LENGTH: 19
<212> TYPE: PRT
<213> ORGANISM: Lama glama

<400> SEQUENCE: 22

Glu Gly Trp Phe Arg Gln Ala Pro Gly Lys Glu Arg Glu Phe Val Ala
1               5                   10                  15

Ala Ile Ser

<210> SEQ ID NO 23
<211> LENGTH: 39
<212> TYPE: PRT
<213> ORGANISM: Lama glama

<400> SEQUENCE: 23

Tyr Tyr Ala Asp Ser Val Lys Gly Arg Phe Thr Ile Ser Arg Asp Asn
1               5                   10                  15

Ala Lys Asn Thr Val Tyr Leu Gln Met Asn Ser Leu Lys Pro Glu Asp
            20                  25                  30

Thr Ala Thr Tyr Tyr Cys Ala
        35

<210> SEQ ID NO 24
<211> LENGTH: 119
<212> TYPE: PRT
<213> ORGANISM: Artificial Sequence
<220> FEATURE:
<223> OTHER INFORMATION: Synthetic single domain
<220> FEATURE:
<221> NAME/KEY: X
<222> LOCATION: (1)..(119)
<223> OTHER INFORMATION: X is any amino acid

<400> SEQUENCE: 24

Met Ala Glu Val Gln Leu Gln Glu Ser Gly Gly Gly Phe Val Gln Ala
1               5                   10                  15

Gly Gly Ser Leu Arg Leu Ser Cys Ala Ala Ser Gly Xaa Xaa Xaa Xaa
            20                  25                  30

Xaa Xaa Xaa Glu Gly Trp Phe Arg Gln Ala Pro Gly Lys Glu Arg Glu
        35                  40                  45

Phe Val Ala Ala Ile Ser Xaa Xaa Xaa Xaa Xaa Xaa Xaa Tyr Tyr Ala
    50                  55                  60
```

```
Asp Ser Val Lys Gly Arg Phe Thr Ile Ser Arg Asp Asn Ala Lys Asn
65                  70                  75                  80

Thr Val Tyr Leu Gln Met Asn Ser Leu Lys Pro Glu Asp Thr Ala Thr
                85                  90                  95

Tyr Tyr Cys Ala Xaa Xaa Xaa Xaa Xaa Xaa Xaa Tyr Trp Gly Gln
            100                 105                 110

Gly Thr Gln Val Thr Ser Ser
            115

<210> SEQ ID NO 25
<211> LENGTH: 119
<212> TYPE: PRT
<213> ORGANISM: Artificial Sequence
<220> FEATURE:
<223> OTHER INFORMATION: Synthetic single domain
<220> FEATURE:
<221> NAME/KEY: X
<222> LOCATION: (1)..(119)
<223> OTHER INFORMATION: X is any amino acid

<400> SEQUENCE: 25

Met Ala Glu Val Gln Leu Gln Ala Ser Gly Gly Gly Phe Val Gln Pro
1               5                   10                  15

Gly Gly Ser Leu Arg Leu Ser Cys Ala Ala Ser Gly Xaa Xaa Xaa Xaa
                20                  25                  30

Xaa Xaa Xaa Met Gly Trp Phe Arg Gln Ala Pro Gly Lys Glu Arg Glu
            35                  40                  45

Phe Val Ser Ala Ile Ser Xaa Xaa Xaa Xaa Xaa Xaa Xaa Tyr Tyr Ala
    50                  55                  60

Asp Ser Val Lys Gly Arg Phe Thr Ile Ser Arg Asp Asn Ser Lys Asn
65                  70                  75                  80

Thr Val Tyr Leu Gln Met Asn Ser Leu Arg Ala Glu Asp Thr Ala Thr
                85                  90                  95

Tyr Tyr Cys Ala Xaa Xaa Xaa Xaa Xaa Xaa Xaa Tyr Trp Gly Gln
            100                 105                 110

Gly Thr Gln Val Thr Ser Ser
            115
```

SYNTHETIC SINGLE DOMAIN ANTIBODY

FIELD OF THE INVENTION

The invention relates to the identification of a highly stable synthetic single domain antibody scaffold and its use in generating synthetic single domain antibody library. The invention also relates to antigen-binding proteins comprising said stable single domain antibody scaffold and their uses, in particular as therapeutics.

BACKGROUND OF THE INVENTION

Over the past decade antibodies imposed themselves as one of the most promising therapeutic approaches, in particular in the field of oncology, as well as an important source of research or diagnosis tools.

The immunoglobulin G (IgG) is the basic structure of a typical antibody, comprising two heterodimers of heavy and light chains bond together by disulphide bridge. Natural single chain antibodies have however been discovered in at least two groups of animals: Camelidae (Hamers-Casterman et al, 1993, Nature, 363, pp 446-448) and sharks (Greenberg et al, Nature. 1995, March 9; 374(6518):168-73). These single chain antibodies constitute an additional class of IgG devoid of light chain. The recognition part of these single chain natural antibodies includes only the variable domain of the heavy chain called VHH. VHHs contain four frameworks (FR) that form the scaffold of the IgG domain and three complementarity-determining regions (CDRs) that are involved in antigen binding.

Many advantages of VHHs scaffold have been reported: without interchain disulfide bridges, they are generally more soluble and stable in a reducing environment (Wesolowski et al, 2009 Med Microbiol Immunol. August; 198(3):157-74). VHH have also been reported to have higher solubility, expression yield and thermostability due to their small size (15 kDa) (Jobling S A et al, Nat Biotechnol. 2003 January; 21 (1): 77-80). Moreover, VHH frameworks show a high sequence and structural homology with human VH domains of family III (Muyldermans et al, 2001. J Biotechnol. June; 74 (4): 277-302) and VHHs have comparable immunogenicity as human VH and thus constitute very interesting agents for therapeutic applications, some of them are currently in phase II clinical trials (Ablynx Nanobodies®). On ten amino acids differing from human, four hallmark aminoacids of VHH have been identified in the framework-2 region.

The properties of VHH scaffolds have many advantages, for use in therapy: they have a better penetration in tissues, a faster clearance in kidneys, a high specificity but also reduced immunogenicity.

Camelid antibody libraries have been described for example in US2006/0246058 (National Research Council of Canada). The described phage display library comprises fragments of llama antibodies, and especially single domain fragments of variable heavy chains (VHH and VH). The libraries were made using lymphocyte genomes of non-immunized animals (naïve library). The resulting phage display library also contains contaminants of conventional VII antibody fragments.

U.S. Pat. No. 7,371,849 (Institute For Antibodies Co., Ltd) also reports methods of making VHH library from VHH genes of camelids. The diversity of such library was obtained by improving the conventional process of isolating VHH variable regions from naïve repertoire.

However, these prior art do not address the issue of immunogenicity from non-human derived antibodies. Even if some of them are identified to bind specific target of interest, they can not be administered in patients for use as therapeutics without the risk of activating the human immune system.

A method to humanize a camelid single-domain antibody is described in Vincke et al, 2008, JBC Vol 284(5) pp 3273-3284.

U.S. Pat. No. 8,367,586 discloses a collection of synthetic antibodies or their fragments. These antibodies comprise variable heavy chain and variable light chain pairs and have, in their framework region, a part of optimal germline gene sequences. This incorporation of human sequence allows to decrease the risk of immunogenicity for therapeutic use.

Monegal et al (2012, Dev Comp Immunol. 36(1):150-6) reports that single domain antibodies with VH hallmarks are repeatedly identified during biopanning of llama naïve libraries. In fact, VH hallmarks are more frequently identified on the binders selected from VHH naïve library, than VHH hallmarks. For example, Monegal et al have shown that 5% of VH hallmarks are round in the naïve library, while 20% of these VH hallmarks are found among the antibodies selected following biopanning against antigens.

Therefore, despite this knowledge, there is still a need to provide single domain antibody libraries, with high diversity, and capable of generating highly stable, humanized single domain antibody with high affinity with a desired target.

Accordingly, one aspect of the disclosure is to provide a non-immune, recombinant single domain antibody library, of high diversity, capable of generating highly stable single domain antibody library with high affinity against specific antigen. Another aspect is to provide a library enriched in single domain antibodies active in the intracellular environment. Yet another aspect is to provide a library enriched in single domain antibodies with high thermostability.

SUMMARY

The purposes of the disclosure are achieved by a method of making a synthetic single domain antibody library, said method comprising the steps of:

i) introducing a diversity of nucleic acids encoding CDR1, CDR2, and CDR3, between the respective framework coding regions of a synthetic single domain antibody (which may be referred to as "hs2dAb" hereafter) to generate a diversity of nucleic acids encoding synthetic single domain antibodies with the same synthetic single domain scaffold amino acid sequence;

wherein said synthetic single domain scaffold amino acid sequence contains at least the following original camelid VHH amino acid residues: F37, E44, R45, F47, and; at least the following humanized amino acid residues: P14, S49, S74, R83, A84, and optionally further comprising the original camelid VHH residues Q5, Q108 and T89.

In one specific embodiment, the synthetic single domain antibody (hs2dAb) derives from VHH of Lama species and comprises the following humanized amino acid residues: F11, P14, S49, S74, K75, V78, Y79, S82b, R83 and A84. In one related specific embodiment, the synthetic single domain antibody may comprise all the following amino acid residues: Q5, A8, F11, P14, F37, K43, E44, R45, F47, S49, A50, S74, K75, V78, Y79, S82b, R83, A84, T89, Q108, wherein the positions of amino acid residues are indicated according to the Kabat nomenclature used for VH and VHH amino acid sequence.

In one specific embodiment, the synthetic single domain antibody comprises the following framework regions consisting of FR1 of SEQ ID NO:1, FR2 of SEQ ID NO:2, FR3 of SEQ ID NO: 3 and FR4 of SEQ ID NO:4, or functional variant framework regions, for example with no more than 1, 2 or 3 conservative amino acid substitutions within each framework region.

In one preferred embodiment, the amino acids residues of the synthetic CDR1 and CDR2 are determined by the following rules:
  at CDR1 position 1: Y, R, S, T, F, G, A, or D;
  at CDR1 position 2: Y, S, T, F, G, T, or T;
  at CDR1 position 3: Y, S, F, or W;
  at CDR1 position 4: Y, R, S, T, F, G, A, W, D, E, K or N;
  at CDR1 position 5: S, T, F, G, A, W, D, E, N, I, H, R, Q, or L;
  at CDR1 position 6: S, T, Y, D, or E;
  at CDR1 position 7: S, T, G, A, D, E, N, I, or V;
  at CDR2 position 1: R, S, F, G, A, W, D, E, or Y;
  at CDR2 position 2: S, T, F, G, A, W, D, E, N, H, R, Q, L or Y;
  at CDR2 position 3: S, T, F, G, A, W, D, E, N, H, Q, P;
  at CDR2 position 4: G, S, T, N, or D;
  at CDR2 position 5: S, T, F, G, A, Y, D, E, N, I, H, R, Q, L, P, V, W, K or M;
  at CDR2 position 6: S, T, F, G, A, Y, D, E, N, I, H, R, Q, L, P, V, W, or K;
  at CDR2 position 7: S, T, F, G, A, Y, D, E, N, I, H, R, Q, L, P, or V;

In one related embodiment that may be combined with the preceding embodiment, said CDR3 amino acid sequence comprises between 9 and 18 amino acids. In one related embodiment that may be combined with the preceding embodiment, said CDR3 amino acid sequence comprises amino acid residues selected among one or more of the following amino acids: S, T, F, G, A, Y, D, E, N, I, H, R, Q, L, P, V, W, K, M.

The disclosure also relates to a synthetic single domain antibody library obtainable by the method described above and comprising at least $3 \cdot 10^9$ distinct single domain antibody coding sequences.

The disclosure further concerns the use of said synthetic single domain antibody library, in a screening method, e.g. phage display, for identifying a synthetic single domain antibody that binds to a target of interest, for example a human protein.

Finally, the disclosure deals with an antigen-binding protein, comprising a synthetic single domain antibody of the following formula: FR1-CDR1-FR2-CDR2-FR3-CDR3-FR4, wherein said framework regions FR1, FR2, FR3, and FR4 contains at least the following original camelid VHH amino acid residues: F37, E44, R45, F47, and, at least the following humanized amino acid residues: P14, S49, S74, R83, A84. Said framework regions may further contain at least the following amino acid residues: Q5, Q108 and T89. In one preferred embodiment, the antigen-binding protein comprises a synthetic single domain antibody with at least the following specific combination of amino acid residues: Q5, A8, F11, P14, F37, K43, E44, R45, F47, S49, A50, S74, K75, V78, Y79, S82b, R83, A84, T89, Q108.

In one specific embodiment which may be combined with the preceding embodiments, the antigen-binding protein comprises a synthetic single domain antibody having one or more of the following functional properties:

a) it can be expressed as soluble single domain antibody in *E. coli* periplasm,
b) it can be expressed as soluble intrabodies in *E. coli*, yeast or other eukaryote cytosol,
c) it is stable in a reducing environment as shown in chloramphenicol acetyl transferase fusion assay,
d) it does not aggregate when expressed in mammalian cells, including as a fusion proteins (e.g. fluorescent protein fusion).

In one preferred embodiment, the framework regions of the antigen-binding protein are derived from VHH framework regions FR1, FR2, FR3, and FR4 of Lama species consisting of FR1 of SEQ ID NO:1, FR2 of SEQ ID NO:2, FR3 of SEQ ID NO: 3 and FR4 of SEQ ID NO:4, or, their functional variants, for example with no more than 0, 1, 2 or 3 conservative amino acid substitutions in each of FR1, FR2, FR3 and FR4.

In another preferred embodiment, which may be combined with the preceding embodiments, the amino acid residues of the synthetic CDR1 and CDR2 are distributed as follows:
  at CDR1 position 1: Y, R, S, T, F, G, A, or D;
  at CDR1 position 2: Y, S, T, F, G, T, or T;
  at CDR1 position 3: Y, S, S, S, F, or W;
  at CDR1 position 4: Y, R, S, T, F, G, A, W, D, E, K or N;
  at CDR1 position 5: S, T, F, G, A, W, D, E, N, I, H, R, Q, or L;
  at CDR1 position 6: S, T, Y, D, or E;
  at CDR1 position 7: S, T, G, A, D, E, N, I, or V;
  at CDR2 position 1: R, S, F, G, A, W, D, E, or Y;
  at CDR2 position 2: S, T, F, G, A, W, D, E, N, H, R, Q, L or Y;
  at CDR2 position 3: S, T, F, G, A, W, D, E, N, H, Q, P;
  at CDR2 position 4: G, S, T, N, or D;
  at CDR2 position 5: S, T, F, G, A, Y, D, E, N, I, H, R, Q, L, P, V, W, K or M;
  at CDR2 position 6: S, T, F, G, A, Y, D, E, N, I, H, R, Q, L, P, V, W, or K;
  at CDR2 position 7: S, T, F, G, A, Y, D, E, N, I, H, R, Q, L, P, or V;
  and the CDR3 amino acid sequence comprises between 9 and 18 amino acids selected among one or more of the following amino acids: S, T, F, G, A, Y, D, E, N, I, H, R, Q, L, P, V, W, K, M.

DETAILED DESCRIPTION

In the present description, positions of amino acid residues in synthetic single domain antibodies or their fragments are indicated according to the Kabat numbering nomenclature as shown hereafter:

TABLE I

| FR or CDR | VL | VH |
|---|---|---|
| FR1 | 1-23 | 1-22 |
| CDR1 | 24-34 | 31-35B |
| FR2 | 35-49 | 36-49 |
| CDR2 | 50-56 | 50-65 |
| FR3 | 57-88 | 66-91 |
| CDR3 | 89-97 | 95-102 |
| FR4 | 98-107 | 103-113 |

The present invention provides a method of making a synthetic single domain antibody library, said method comprising i. introducing a diversity of synthetic nucleic acids encoding CDR1, CDR2, and CDR3, between the respective framework coding regions of a synthetic single domain antibody to generate nucleic acids encoding a diversity of synthetic single domain antibodies with the same synthetic single domain antibody scaffold amino acid sequence, wherein said synthetic single domain scaffold amino acid sequence contains at least the following original camelid VHH amino acid residues: F37, E44, R45, F47, and; at least the following humanized amino acid residues: P14, S49, S74, R83, A84, and optionally further comprising the original camelid VHH residues Q5, Q108 and T89.

The Synthetic Single Domain Antibody Scaffold of the Invention

The invention relates to the identification of unique features in framework regions of single domain antibodies, for obtaining a highly stable single domain antibody scaffold and its use in generating synthetic single domain antibody library, such as synthetic single domain antibody phage display library. The resulting hs2dAb with said unique scaffold are highly stable and have low risks of immunogenicity.

As a starting material for making the library, a nucleic acid encoding single domain antibody may be provided.

As used herein, the term "single domain antibody" refers to an antibody fragment with a molecular weight of only 12-15 kDa, consisting of a single monomeric variable antibody domain derived from a heavy chain. Said single domain antibody may derive from fragment of natural occurring antibodies devoid of light chains, such as so called VHH antibodies derived from camelid antibodies or so called VNAR fragments derived from shark species antibody. Said single domain antibody may also derive from human antibodies with specific following mutations: F37, E44, R45, and F47. Single domain antibody thus contains at least 4 framework regions interspaced by 3 hypervariable CDR regions, resulting in the following typical antibody variable domain structure: FR1-CDR1-FR2-CDR2-FR3-CDR3-FR4. Said single domain does not interact with light chain antibody variable region to form conventional heterodimer of heavy and light chains antigen-binding VH structure.

As used herein, the term "synthetic" means that such antibody has not been obtained from fragments of naturally occurring antibodies but produced from recombinant nucleic acids comprising artificial coding sequences.

In particular, the synthetic single domain antibody libraries of the disclosure have been generated by synthesis of artificial framework and CDR coding sequences. As opposed to libraries obtained by amplification of naïve repertoire from non-immunized llama animals, the synthetic single domain antibody library of the invention does not contain conventional VH antibody.

Advantageously, in one preferred embodiment of the synthetic single domain antibody library of the present invention, all single domain antibody clones contain the same framework regions, thereby providing a unique synthetic single domain antibody scaffold.

As used herein, the term "scaffold" refers to the 4 framework regions of the synthetic single domain antibodies of the library of the invention. Typically, all single domain antibodies of a library of the invention have the same scaffold amino acid sequences while their CDRs may be different (the diversity of each library is only in the CDR regions).

The synthetic single domain antibody scaffold according to the present disclosure contains at least the following original camelid VHH amino acid residues: F37, E44, R45, F47, and; at least the following humanized amino acid residues: P14, S49, S74, R83, A84. Said synthetic single domain scaffold of the present invention may optionally further comprise the original camelid VHH residues Q5, Q108 and T89. Such unique features provide highly stable synthetic single domain antibody with low risk of immunogenicity.

In one specific embodiment, the synthetic single domain antibody scaffold is obtained by mutagenizing a coding sequence of VHH of Lama species scaffold antibody in order to obtain at least the following humanized amino acid residues in the amino acid sequence: P14, S49, S74, R83, A84, and preferably, the following humanized amino acid residues: F11, P14, S49, S74, K75, V78, Y79, S82b, R83 and A84.

In one specific embodiment that may be combined with the preceding embodiment, the synthetic single domain antibody scaffold comprises
  (i) a FR2 amino acid sequence that is identical to germline Llama FR2 amino acid sequence;
  (ii) a FR3 amino acid sequence that is identical to germline human FR3 (VH3) amino acid sequence; and,
  (iii) a FR4 amino acid sequence that is identical to germline Llama FR4 amino acid sequence.

In one specific embodiment that may be combined with the preceding embodiments, the synthetic single domain antibody scaffold thus comprises the following specific combination of amino acid residues: Q5, A8, F11, P14, F37, K43, E44, R45, F47, S49, A50, S74, K75, V78, Y79, S82b, R83, A84, T89, Q108.

In another specific embodiment, the synthetic single domain antibody scaffold comprises the following framework regions consisting of FR1 of SEQ ID NO:1, FR2 of SEQ ID NO:2, FR3 of SEQ ID NO: 3 and FR4 of SEQ ID NO:4, or functional variant framework regions, for example with no more than 1, 2 or 3 conservative amino acid substitutions within each framework region, more preferably, within only one framework region.

An example of a synthetic single domain antibody scaffold is shown in FIG. 1.

Conservative amino acid substitutions are ones in which the amino acid residue is replaced with an amino acid residue having a similar side chain. Families of amino acid residues having similar side chains have been defined in the art. These families include amino acids with basic side chains (e.g. lysine, arginine, histidine), acidic side chains (e.g. aspartic acid, glutamic acid), uncharged polar side chains (e.g. glycine, asparagine, glutamine, serine, threonine, tyrosine, cysteine, tryptophan), nonpolar side chains (e.g. alanine, valine, leucine, isoleucine, proline, phenylalanine, methionine), beta-branched side chains (e.g. threonine, valine, isoleucine) and aromatic side chains (e.g. tyrosine, phenylalanine, tryptophan, histidine).

In another embodiment, the synthetic single domain antibody scaffold comprises functional variants of FR1, FR2, FR3 and FR4 framework regions having at least 90%, preferably 95% identity to SEQ ID NOs1-4 respectively.

As used herein, the percent identity between two sequences is a function of the number of identical positions shared by the sequences (i.e., % identity=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described below.

The percent identity between two amino acid sequences can be determined using the algorithm of E. Myers and W. Miller (Comput. Appl. Biosci. 4: 1 1-17, 1988) which has been incorporated into the ALIGN program. In addition, the percent identity between two amino acid sequences can be determined using the Needleman and Wunsch (J. Mol. Biol. 48:443-453, 1970) algorithm which has been incorporated into the GAP program in the GCG software package. Yet another program to determine percent identity is CLUSTAL (M. Larkin ef a/., Bioinformatics 23.2947-2948, 2007; first described by D. Higgins and P. Sharp, Gene 73:237-244, 1988) which is available as stand-alone program or via web servers (see http://www.clustal.org/).

Functional variants may be tested for their capacity to retain the advantageous properties of said synthetic single domain scaffold of the present invention. In particular, they may be tested for their capacity to retain at least one or more of the following properties:
  i. it can be expressed as soluble single domain antibody in E. coli periplasm,
  ii. it can be expressed as soluble intrabodies in E. coli, yeast or other eukaryote cytosol,
  iii. it is stable in reducing environment in chloramphenicol acetyl transferase fusion assay,
  iv. it does not aggregate when expressed in mammalian cells, including as a fusion proteins (e.g. fluorescent protein fusion).

Assays for testing the above properties are described in the Examples.

For example, a reference synthetic single domain antibody coding sequence is constructed by grafting reference CDRs coding sequences (such as the CDRs of clone D10 of SEQ ID NO:9) into a variant scaffold coding sequence to be tested (with homologous sequences to SEQ ID NOs 1-4). This reference synthetic single domain antibody coding sequence allows to produce a reference synthetic single domain antibody which can be assayed for the above properties.

Introduction of CDR Diversity in the Selected Single Domain Antibody Scaffold

Methods for generating CDRs diversity for antibody libraries, in particular by random or directed synthesis of CDR coding sequences and cloning into corresponding framework sequences have been widely described in the art.

The synthetic single domain antibody libraries of the present disclosure are generated similarly by introducing CDR high diversity into the unique selected scaffold sequence, for example, as described in Lindner, T., H. Kolmar, U. Haberkorn, and W. Mier. 2011. Molecules. 16:1625-1641.

In one preferred embodiment of the present disclosure, the position of each amino acid sequence of synthetic CDR1 and CDR2 is rationally designed to mimic natural diversity of CDRs in human repertoire.

Cysteines are voluntarily avoided because of their thiol groups which may interfere with intracellular expression and functionality. Besides, arginine and hydrophobic residues may also be avoided because of the high risk aggregation of the resulting antibody. A low proline rate is also preferred because it provides more flexibility in the CDRs. Preferably, serine, threonine and tyrosine are the most frequent residues in all three CDRs, as being involved in bonds with the epitope. Aspartate and glutamate may also be enriched at some positions in order to increase solubility. For CDR3 sequences, the lengths may influence the binding potential to different epitope shape, in particular cavity. Therefore, different lengths of CDR3 sequences may be introduced into the libraries.

In one specific embodiment, the skilled person may select the amino acid residues of the synthetic CDR1 and CDR2 according to the following rules:
  at CDR1 position 1: Y, R, S, T, F, G, A, or D;
  at CDR1 position 2: Y, S, T, F, G, T, or T;
  at CDR1 position 3: Y, S, F, or W;
  at CDR1 position 4: Y, R, S, T, F, G, A, W, D, E, K or N;
  at CDR1 position 5: S, T, F, G, A, W, D, E, N, I, H, R, Q, or L;
  at CDR1 position 6: S, T, Y, D, or E;
  at CDR1 position 7: S, T, G, A, D, E, N, I, or V;
  at CDR2 position 1: R, S, F, G, A, W, D, E, or Y;
  at CDR2 position 2: S, T, F, G, A, W, D, E, N, H, R, Q, L or Y;
  at CDR2 position 3: S, T, F, G, A, W, D, E, N, H, Q, P;
  at CDR2 position 4: G, S, T, N, or D;
  at CDR2 position 5: S, T, F, G, A, Y, D, E, N, I, H, R, Q, L, P, V, W, K or M;
  at CDR2 position 6: S, T, F, G, A, Y, D, E, N, I, H, R, Q, L, P, V, W, or K;
  at CDR2 position 7: S, T, F, G, A, Y, D, E, N, I, H, R, Q, L, P, or V;

Furthermore, in another specific embodiment, CDR3 amino acid sequence comprises between 9 and 18 amino acids selected among one or more of the following amino acids: S, T, F, G, A, Y, D, E, N, I, H, R, Q, L, P, V, W, K, M.

The above rules of occurrence are used as a guidance for generating preferred libraries of the invention, however, other libraries with different occurrence rules are also part of the invention, as long as they contain the advantageous synthetic single domain antibody scaffold of the present invention.

In specific embodiments, only a significant proportion of the clones of the library may follow strictly the above rules of occurrence. For example, statistically, at least 50%, 60%, 70%, 80% or at least 90% of the clones of the library follow the above rules of occurrence of amino acid residues in CDR1, CDR2 and CDR3 positions.

In order to respect these occurrences of amino acid positions, and to avoid the occurrence of in frame stop, or cysteine or reduce frameshift, advanced gene synthesis approaches are preferably used. These methods encompass, but are not limited to, double strand DNA triple blocks as described in Van den Brulle et al., 2008. Biotechniques 45(3): 340-3, tri-nucleotide synthesis, or other codon-controlled and more generally position-controlled degenerate synthesis approaches.

In specific embodiments, codon bias may further be optimized for example for host cell species, for example, mammalian host cells expression, using well known methods.

In one specific embodiment, the coding sequence is designed so that it does not contain undesired restriction sites, for example, restriction sites that are used for cloning the coding sequence into the appropriate cloning or expression vector.

The resulting diverse coding sequences are introduced into a suitable expression or cloning vectors for antibody libraries. In a specific embodiment, the expression vector is a plasmid. In another preferred embodiment, the expression vector is suitable for generating phage display libraries. Two different types of vectors may be used for generating phage display libraries: phagemid vectors and phage vectors.

Phagemids are derived from filamentous phage (Ff-phage-derived) vectors, containing the replication origin of a plasmid. The basic components of a phagemid mainly include the replication origin of a plasmid, the selective marker, the intergenic region (IG region, usually contains the packing sequence and replication origin of minus and plus strands), a gene of a phage coat protein, restriction enzyme recognition sites, a promoter and a DNA segment encoding a signal peptide. Additionally, a molecular tag can be included to facilitate screening of phagemid-based library. Phagemids can be convened to filamentous phage particles with the same morphology as Ff phage by co-infection with the helper phages, such as R408, M13KO7 and VCSM13 (Stratagene). One example of phage vector is fd-tet (Zacher et al, gene, 1980, 9, 127-140) which consists of fd-phage genome and a segment of Tn10 inserted near the phage genome origin of replication. Examples of promoters for use in phagemid vectors include, without limitation, PlacZ or PT7, examples of signal peptide includes without limitation pelB leader, gIII, CAT leader, SRP or OmpA signal peptide.

Other phage-display methods use lytic phages like T4 or T7. Vectors other than phages may also be used to generate display libraries, including vectors for bacterial cell display (Daugherty et al., 1999 Protein Eng. July; 12(7):613-21, Georgiou et al., 1997 Nat Biotechnol. 1997 January; 15(1): 29-34), yeast cell display (Boder and Wittrup, Nat Biotechnol. 1997 June; 15(6):553-7) or ribosome display (Zahnd C. Amstutz P. Plückthun A. Nat Methods. 2007 March; 4(3): 269-79). DNA display (Eldridge et al., Protein Engineering. Design & Selection vol. 22 no. 11 pp. 691-698, 2009) and surface display on mammalian cells (Rode H J, et al. Biotechniques. 1996 October; 21(4):650, 652-3, 655-6, 658) have also been reported. Non display methods like yeast two-hybrid may also be used to select relevant binders from the library (Visintin et al., 1999 Proc Natl Acad Sci USA 96, 11723-11728.).

In one preferred embodiment, in order to avoid generating empty vectors, positive selection of recombinant coding sequence in the cloning vectors bearing a suicide gene is applied (see for example Philippe Bernard, 1996, BioTechniques, Vol 21, No 2 "Positive Selection of Recombinant DNA by CcdB").

Preferably, the theoretical diversity as calculated by all possible combination of CDR amino acid residues as designed for generating the antibody library is at least $10^{11}$ or at least $10^{11}$ unique sequences.

Synthetic Single Domain Antibody Library of the Invention and their Use

Consequently, according to another aspect, the disclosure relates to a synthetic single domain antibody library obtainable or obtained by the previous method.

As used herein, the term "synthetic single domain antibody library" thus encompasses nucleic acid libraries comprising said synthetic single domain antibody coding sequences with high diversity, optionally included in a cloning vector or expression vector. The term "synthetic single domain antibody library" further includes any transformed host cells or organisms, with said nucleic acid libraries, and more specifically, bacterial, yeast or filamentous fungi, or mammalian cells transformed with said nucleic acid libraries, or bacteriophages or viruses containing said nucleic acid libraries. The term "synthetic single domain antibody library" further includes the corresponding mixture of diverse antibodies encoded by said nucleic acid library. As used herein, the term "clone" will refer to each unique individual of the antibody library, whether, nucleic acids, host cells, or single domain antibodies.

In one specific embodiment of the disclosure, the synthetic single domain antibody library of the present disclosure comprises at least $3 \cdot 10^9$ diverse clones.

This library may be used in a screening method, for identifying a synthetic single domain antibody that binds specifically to a target of interest. Any known screening methods for identifying binders with specific affinity to a target of interest may be used with the synthetic single domain antibody libraries of the invention. Such methods include without limitation phage display technologies, bacterial cell display, yeast cell display, mammalian cell display or ribosome display.

Preferably, the screening method is the phage display.

Preferably, the target of interest is a therapeutic target, and the synthetic single domain antibody library is used to identify synthetic single domain antibody with specific binding to said therapeutic target. In specific embodiments, the target of interest comprises at least an antigenic determinant. In specific embodiments, the target is a saccharide or polysaccharide, a protein or glycoprotein, a lipid. In one specific embodiment, said target of interest is of plant, yeast, fungus, insect, mammalian or other eukaryote cell origins. In another specific embodiment, said target of interest is of bacterial, protozoan or viral origin.

In one specific embodiment. "a single domain antibody that binds specifically to a target of interest" is intended to refer to single domain antibody that binds to the target of interest with a $K_D$ of 1 mM or less. 100 µM or less. 101 µM or less. This does not exclude that said single domain antibody also binds to other antigens.

The term "$K_D$", as used herein, is intended to refer to the dissociation constant, which is obtained from the ratio of $K_d$ to $K_a$ (i.e. $K_d/K_a$) and is expressed as a molar concentration$^{-1}$ ($M^{-1}$). $K_D$ values for antibodies can be determined using methods well established in the art. A method for determining the $K_D$ of an antibody is by using surface plasmon resonance, or using a biosensor system such as a Biacore® system or Proteon®.

Antigen-Binding Protein of the Invention

Considering the high diversity of the synthetic single domain antibody libraries of the invention, the skilled person can obtain synthetic single domain antibody with high affinity and high specificity to a target of interest, by conventional screening methods, such a phage display.

The resulting synthetic single domain antibody can then be further modified for generating appropriate antigen-binding protein. In particular, the CDR residues may be modified for example to increase the antibody affinity to the target of interest, improve its folding or its production, using technologies known in the art (mutagenesis, affinity maturation).

Accordingly, another aspect of the invention further relates to an antigen-binding protein, comprising a synthetic single domain antibody of the following formula: FR1-CDR1-FR2-CDR2-FR3-CDR3-FR4, wherein said framework regions FR1, FR2, FR3, and FR4 contains at least the following original camelids VHH amino acid residues: F37, E44, R45, F47, and; at least the following humanized amino acid residues: P14, S49, S74, R83, A84.

In one embodiment, the framework regions further contain at least the following amino acid residues: Q5, Q108 and T89. In another embodiment, the synthetic single domain antibody comprises the specific combination of at least the following amino acid residues: Q5, A8, F11, P14, F37, K43, E44, R45, F47, S49, A50, S74, K75, V78, Y79, S82b, R83, A84, T89, Q108.

In one preferred embodiment, the framework regions are derived from VHH framework regions FR1, FR2, FR3, and FR4 of Lama species. In another specific embodiment, the single domain antibody scaffold comprises
  (i) a FR2 amino acid sequence that is identical to germline Llama FR2 amino acid sequence;
  (ii) a FR3 amino acid sequence that is identical to germline FR3 (V113) amino acid sequence; and,
  (iii) a FR4 amino acid sequence that is identical to germline Llama FR4 amino acid sequence.

In one preferred embodiment, the synthetic single domain antibody comprises either of the following features:
(i) framework regions FR1 of SEQ ID NO:1, FR2 of SEQ ID NO:2, FR3 of SEQ ID NO:3, and FR4 of SEQ ID NO:4,
(ii) functional variant framework regions having no more 1, 2 or 3 amino acid conservative substitutions and retaining advantageous synthetic single domain properties,
(iii) functional variant framework regions FR1, FR2, FR3 and FR4 having at least 60, 70, 80, 90, 95, 96, 97, 98, or 99 percent sequence identity to SEQ ID NOs:1-4 respectively and retaining advantageous synthetic single domain properties.

Typically, one or more amino acid residues within the framework regions can be replaced with other amino acid residues from the same side chain family, and the new polypeptide variant can be tested for retained advantageous properties using the functional assays described herein.

Such advantageous properties are one or more of the following properties:
  i. it can be expressed as soluble single domain antibody in E. coli periplasm Typically, a yield exceeding 5 mg/L with a pelB leader peptide may be preferably obtained in E. coli strains.
  ii. it can be expressed as soluble intrabodies in E. coli cytosol For example, antibodies may be expressed in E. coli strains BL21(DE3) at a yield exceeding 50 mg/liter with a T7 promoter.
  iii. it is stable in a reducing environment as shown in chloramphenicol acetyl transferase fusion assay Functional assays for the above properties are described in the Examples. The bacterial cells expressing said antigen-binding protein containing the synthetic single domain antibody of the invention in fusion with chloramphenicol acetyl transferase as a C-terminal tag should be resistant to chloramphenicol, in particular, at a concentration of chloramphenicol higher than 300 μg/ml in culture medium.
  iv. it does not aggregate when expressed in mammalian cell lines as fluorescent protein fusions.

Preferably, no aggregation should be detected when the antigen-binding protein containing the synthetic single domain antibody is expressed as fluorescent protein fusion.

Preferably, the amino acid residues of the synthetic CDR1 and CDR2 may be:
  at CDR1 position 1: Y, R, S, T, F, G, A, or D;
  at CDR1 position 2: Y, S, T, F, G, T, or T;
  at CDR1 position 3: Y, S, S, S, F, or W;
  at CDR1 position 4: Y, R, S, T, F, G, A, W, D, E, K or N;
  at CDR1 position 5: S, T, F, G, A, W, D, E, N, I, H, R, Q, or L;
  at CDR1 position 6: S, T, Y, D, or E;
  at CDR1 position 7: S, T, G, A, D, E, N, I, or V;
  at CDR2 position 1: R, S, F, G, A, W, D, E, or Y;
  at CDR2 position 2: S, T, F, G, A, W, D, E, N, H, R, Q, L or Y;
  at CDR2 position 3: S, T, F, G, A, W, D, E, N, H, Q, P;
  at CDR2 position 4: G, S, T, N, or D;
  at CDR2 position 5: S, T, F, G, A, Y, D, E, N, I, H, R, Q, L, P, V, W, K or M;
  at CDR2 position 6: S, T, F, G, A, Y, D, E, N, I, H, R, Q, L, P, V, W, or K;
  at CDR2 position 7: S, T, F, G, A, Y, D, E, N, I, H, R, Q, L, P, or V;
and CDR3 amino acid sequence comprises between 9 and 18 amino acids selected among one or more of the following amino acids: S, T, F, G, A, Y, D, E, N, I, H, R, Q, L, P, V, W, K, M.

Accordingly, in one preferred embodiment, the antigen-binding protein of the invention, essentially consists of a synthetic single domain antibody of the general formula FR1-CDR1-FR2-CDR2-FR3-CDR3-FR4. In such embodiment, more preferably, FR1 is SEQ ID NO:1, or a functional variant of SEQ ID NO:1 with 1, 2 or 3 amino acid substitutions. FR2 is SEQ ID NO:2, or a functional variant of SEQ ID NO:2 with 1, 2 or 3 amino acid substitutions; FR3 is SEQ ID NO:3, or a functional variant of SEQ ID NO:3 with 1, 2 or 3 amino acid substitutions; FR4 is SEQ ID NO:4, or a functional variant of SEQ ID NO:4 with 1, 2 or 3 amino acid substitutions; CDR1, CDR2 amino acid sequences have amino acid residues as follows:
  at CDR1 position 1: Y, R, S, T, F, G, A, or D;
  at CDR1 position 2: Y, S, T, F, G, T, or T;
  at CDR1 position 3: Y, S, S, S, F, or W;
  at CDR1 position 4: Y, R, S, T, F, G, A, W, D, E, K or N;
  at CDR1 position 5: S, T, F, G, A, W, D, E, N, I, H, R, Q, or L;
  at CDR1 position 6: S, T, Y, D, or E;
  at CDR1 position 7: S, T, G, A, D, E, N, I, or V;
  at CDR2 position 1: R, S, F, G, A, W, D, E, or Y;
  at CDR2 position 2: S, T, F, G, A, W, D, E, N, H, R, Q, L or Y;
  at CDR2 position 3: S, T, F, G, A, W, D, E, N, H, Q, P;
  at CDR2 position 4: G, S, T, N, or D;
  at CDR2 position 5: S, T, F, G, A, Y, D, E, N, I, H, R, Q, L, P, V, W, K or M;
  at CDR2 position 6: S, T, F, G, A, Y, D, E, N, I, H, R, Q, L, P, V, W, or K;
  at CDR2 position 7: S, T, F, G, A, Y, D, E, N, I, H, R, Q, L, P, or V;
and CDR3 amino acid sequence comprises between 9 and 18 amino acids selected among one or more of the following amino acids: S, T, F, G, A, Y, D, E, N, I, H, R, Q, L, P, V, W, K, M.

Another aspect of the disclosure pertains to nucleic acid molecules that encode the antigen-binding proteins of the disclosure. The disclosure thus provides an isolated nucleic acid encoding at least said synthetic single domain antibody portion of the antigen-binding protein.

The nucleic acids may be present in whole cells, in a cell lysate, or may be nucleic acids in a partially purified or substantially pure form. A nucleic acid is "isolated" or "rendered substantially pure" when purified away from other cellular components or other contaminants, e.g. other cellular nucleic acids or proteins, by standard techniques, including alkaline/SDS treatment, CsCI banding, column chromatography, agarose gel electrophoresis and others well known in the art. See, F. Ausubel, et al., ed. 1987 Current Protocols in Molecular Biology, Greene Publishing and Wiley Interscience, New York. A nucleic acid of the invention can be, for example, DNA or RNA and may or may not contain intronic sequences.

In an embodiment, the nucleic acid is a DNA molecule. The nucleic acid may be present in a vector such as a phage display vector, or in a recombinant plasmid vector. In one specific embodiment, the invention thus provides an isolated nucleic acid or a cloning or expression vector comprising at least one or more of the following nucleic acid sequences: SEQ ID NO:5, SEQ ID NO:6, SEQ ID NO:7, SEQ ID NO:8, encoding respectively framework regions FR1, FR2, FR3 and FR4 of SEQ ID NOs 1-4, or variant corresponding sequences with at least 90% identity to said SEQ ID NOs 5-8, encoding functional variants of FR1, FR2, FR3, and FR4 of SEQ ID NOs 1-4.

DNA fragments encoding the antigen-binding proteins, as described above and in the Examples, can be further manipulated by standard recombinant DNA techniques, for example to include any signal sequence for appropriate secretion in expression system, any purification tag and cleavable tag for further purification steps. In these manipulations, a DNA fragment is operatively linked to another DNA molecule, or to a fragment encoding another protein, such as a purification/secretion tag or a flexible linker. The term "operatively linked", as used in this context, is intended to mean that the two DNA fragments are joined in a functional manner, for example, such that the amino acid sequences encoded by the two DNA fragments remain in-frame, or such that the protein is expressed under control of a desired promoter.

The antigen-binding proteins of the disclosure can be produced in a host cell transfectoma using, for example, a combination of recombinant DNA techniques and gene transfection methods as is well known in the art. For expressing and producing recombinant antigen-binding proteins of the invention in host cell transfectoma, the skilled person can advantageously use its own general knowledge related to the expression and recombinant production of antibody molecules or single domain antibody molecules.

The disclosure thus provides a recombinant host cell suitable for the production of said antigen-binding proteins of the invention, comprising the nucleic acids, and optionally, secretion signals. In a preferred aspect the host cell of the invention is a mammalian cell line. The invention further provides a process for the production of an antigen-binding protein, as described previously, comprising culturing the host cell under appropriate conditions for the production of the antigen-binding protein, and isolating said protein.

Mammalian host cells for secreting the antigen-binding proteins of the disclosure, include CHO, such as dhfr-CHO cells, (described by Urlaub and Chasin, 1980, Proc. Natl. Acad. Sci. USA 77:4216-4220) used with a DHFR selectable marker, e.g. as described in R. J. Kaufman and P. A. Sharp, 1982 Mol. Biol. 159:601-621, NSO myeloma cells, or the pFuse expression system from Invivogen, as described in Moutel, S., El Majou, A., Vielemeyer, O., Nizak, C., Benaroch, P., Dubel, S., and Perez, F. (2009). A multi-Fc-species system for recombinant antibody production. BMC Biotechnol 9, 14, COS cells and SP2 cells or human cell lines (including PER-C6 cell lines, Crucell or HEK293 cells, Yves Durocher et al., 2002, Nucleic acids research vol. 30, No 2 p9). When said nucleic acids encoding antigen-binding proteins of the invention are introduced into mammalian host cells, the antigen-binding proteins are produced by culturing the host cells for a period of time sufficient to allow for expression of the recombinant polypeptides in the host cells or secretion of the recombinant polypeptides into the culture medium in which the host cells are grown and proper refolding to produce said antigen-binding proteins.

The antigen-binding protein can then be recovered from the culture medium using standard protein purification methods.

In one specific embodiment, the present disclosure provides multivalent antigen-binding proteins of the invention, for example in the form of a complex, comprising at least two identical or different synthetic single domain antibody amino acid sequences of the invention. In one embodiment, the multivalent protein comprises at least two, three or four synthetic single domain antibody amino acid sequences. The synthetic single domain amino acid sequences can be linked together via protein fusion or covalent or non-covalent linkages.

In another aspect, the present disclosure provides a composition. e.g. a pharmaceutical composition, containing one or a combination of the antigen-binding proteins of the present invention, formulated together with one or more pharmaceutically acceptable vehicles or carriers.

Pharmaceutical formulations of the disclosure may be prepared for storage by mixing the proteins having the desired degree of purity with optional physiologically acceptable carriers, excipients or stabilizers (Remington: The Science and Practice of Pharmacy 20th edition (2000)), in the form of aqueous solutions, lyophilized or other dried formulations.

Examples of suitable aqueous and nonaqueous carriers that may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as, aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage.

In the following, the disclosure will be illustrated by means of the following examples and figures.

FIGURES LEGENDS

FIG. 1A-C. (A). Chloramphenicol acetyl transferase carboxy terminal fusion is a folding reporter allowing the selection of soluble amino terminal VHH. Scheme of the construct expressed from pAO-VHH-CATHa vector (B) Relative colony growth of selected VHH on chloramphenicol selection medium (Cam). (C) Amino acid sequences alignment of the lama scaffold IsdAb with the humanized synthetic scaffold of the library hs2dAb. Positions (IMGT numbering) were highlighted according to amino acids conserved from the D10 intrabody scaffold for intrinsic solubility properties of VHH (black) and humanized residues conserved with human conventional VH3 (Grey).

FIG. 2A-D (A) Phages presenting both scaffold were produced in E. coli and supernatant were detected in Western Blot with an anti-pIII antibody (Biolabs). Two bands are visible, one for pIII and one for the fusion with single domains. (B) Production of both scaffolds in E. coli or in CHO cells analysed by Dot Blot. Serial dilutions of supernatant were revealed with an anti-HisTag antibody (Sigma). (C) Immunofluorescence of HeLa cells with recombinant Ab from both scaffolds labelling the nuclear rim structure characteristic of the nuclear lamina. (D) HeLa cells were transiently transfected with the GFP-fused anti-Lamin antibodies expression plasmids and live cells were imaged after 24 h. This showed that both synthetic antibody scaffold anable the recognition of the intracellular lamin target.

Figure 3B:
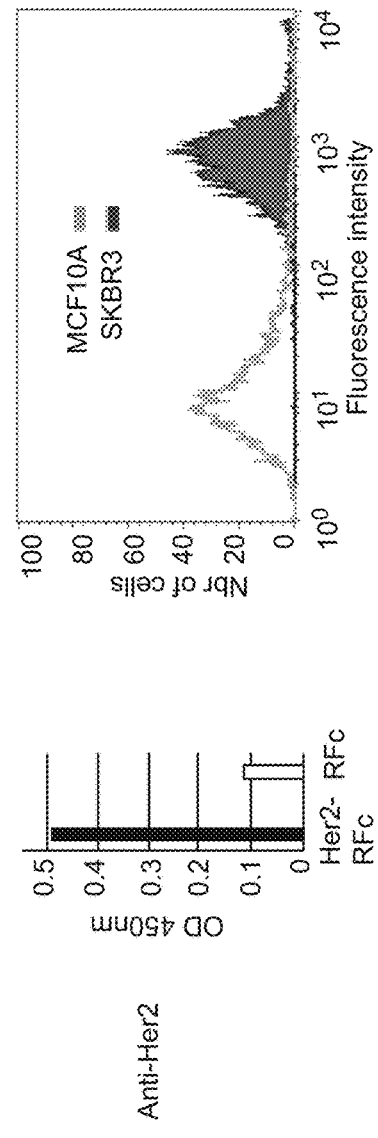
Figure 3C:
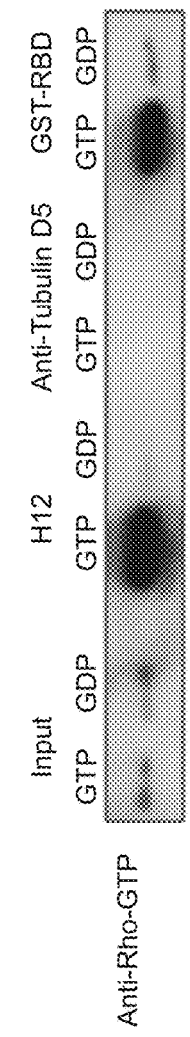

FIG. 3A-C (A) s2dAb D5 stained microtubules by immunofluorescence in HeLa cells. Cells were fixed and stained with a VHH revealed by an anti-HisTag (Sigma) and an anti-MouseCy3 secondary antibody (Jackson). D5 detect also tubulin in Western blot experiment with HeLa cell extracts revealed with HRP secondary antibody (Jackson). (B) Phage ELISA of clone D10 anti-Her2 on Her2 fused with a rabbit Fc versus binding on rabbit Fc at equimolar concentration. FACS analysis of HD10 anti-Her2 on SKBR3 Her2 positive cells versus MCF10A Her2 negative cells. (C) H12 is a conformational antibody binding only to the GTP bound, activated state of RhoA GTPase. A CBD tagged H12 pull down from HeLa cell extract loaded with either 100 µM GTP gamma S (GTP) or with 1 mM GDP as inputs. Western blot experiment reveals RhoA at similar level in 5% of both input but only on the GTP loaded extract in the CBD-H12 pull down. D5 anti tubulin is a negative control and the conventional GST-RBD (Rho binding domain of Rhotekin) is shown as a positive control of active Rho pull down.

Figure 4A:
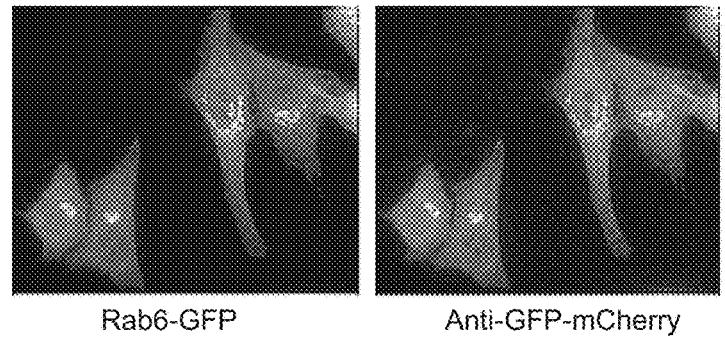
Figure 4B:
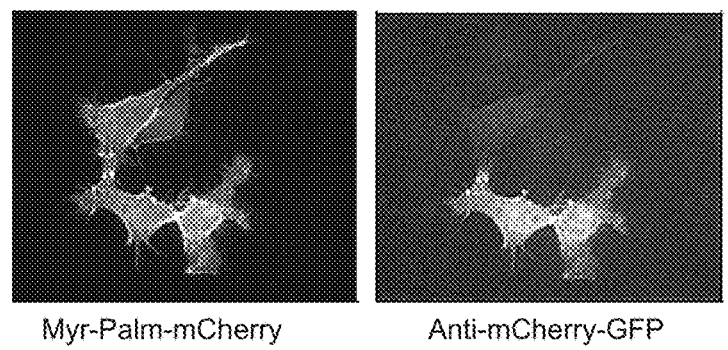
Figure 4C:
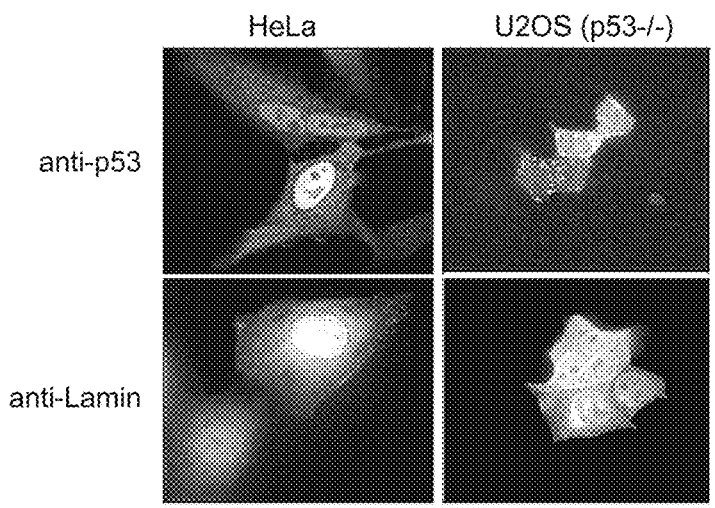

FIG. 4A-C Intracellular expression of hs2dAb. (A) HeLa cells were cotransfected with GFP tagged Rab6 and mCherry-tagged hs2dAb anti-GFP plasmids. The hs2dAb-mCherry anti-GFP interacted with its target in vivo and the mCherry signal colocalized perfectly with the GFP-Rab6 one. (B)) HeLa cells were cotransfected with Myr-palm-mCherry and a hs2dAb-GFP anti-mCherry plasmids. The hs2dAb-GFP anti-mCherry interacted with its target in vivo and colocalized perfectly with the mCherry localized at the plasma membrane. (C) Hela cells (p53+/+) and U2OS (p53-/-) cells were transfected either with a hs2dAb-mCherry anti-p53 antibody or with a hs2dAb-mCherry anti-Lamin. While the anti-Lamin intrabody labelled both cells types, the anti-p53 intrabody labelled only the nuclei of p53-positive cells.

Figure 5:
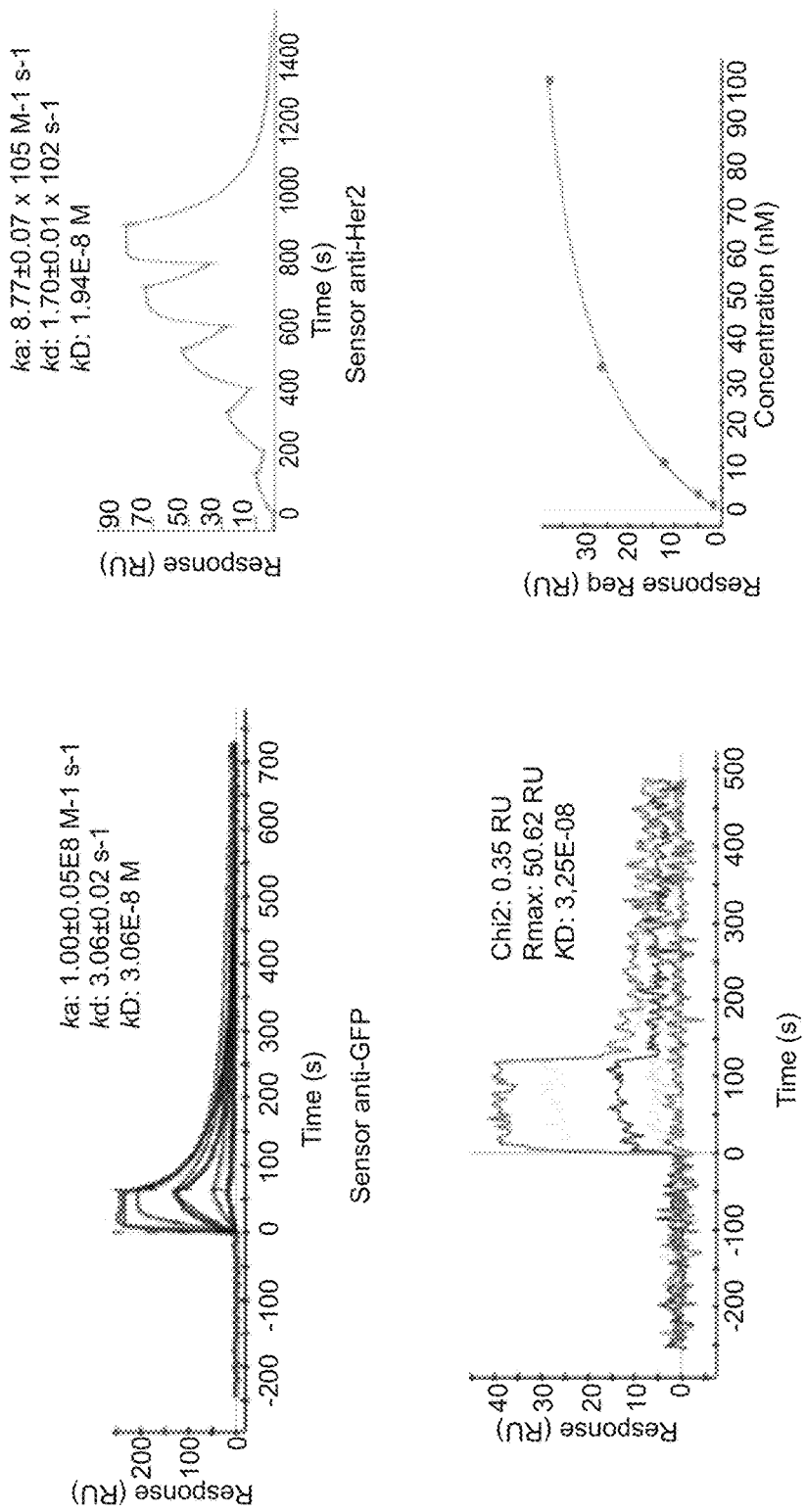

FIG. 5 Sensorgrams for the binding of hs2dAb anti-GFP, anti-p53 and anti-Her2 on immobilized antigens. Different concentrations of hs2dAb were loaded at 25° C. and fitted with a 1:1 langmuir interaction model.

EXAMPLES

Functional Assays
Soluble Expression in E. coli Periplasm

Single domain antibody fragments were subcloned in a pHEN6 derived bacterial periplasm expression vector and expressed downstream of the pelB secretion sequence. Freshly transform colonies were grown in Terrific Broth medium supplemented with 1% glucose and 30 µg/ml kanamycin antibiotic until A600=0.6-0.8 was reached. The expression of antibody fragment tagged with 6 His was then induced with 500 µM isopropyl β-D-thiogalactopyranoside for 16 h at 28° C. then span down. After centrifugation, the cell pellets were incubated in Tris-EDTA-Sucrose osmotic shock buffer and centrifuged again. The cell lysates were cleared and loaded onto an IMAC resin affinity column for poly Histidine tag. The eluted fraction was dialyzed, and the purity of the protein was analyzed by SDS-PAGE.

Soluble Expression of Intrabodies in E. coli Cytosol

Single domain antibody fragments were subcloned in a bacterial expression vector under the control of a T7 promoter. The plasmid constructs were transformed into E. coli BL21(DE3) cells. Single colonies were grown in LB medium supplemented with 1% glucose and 30 µg/ml kanamycin antibiotic until A600=0.6-0.8 was reached. Antibody fragment expression was then induced with 500 µM isopropyl β-D-thiogalactopyranoside for 6 h to 8 h at 28° C. then span down. After centrifugation, the cell pellets were lysed and centrifuged again. The cell lysates were cleared and loaded onto an IMAC resin affinity column for poly Histidine tag. The eluted fraction was dialyzed, and the purity of the protein was analyzed by SDS-PAGE.

Chloramphenicol Acetyl Transferase Fusion Assay

Single domain antibody fragments were subcloned in the pAOCAT bacterial periplasm expression vector. Chloramphenicol resistance assay was performed using BL21(DE3) cells transformed with the pAOCAT-VHH fusion constructs. Bacteria were used for inoculating 500 µL of LB containing kanamycin (35 µg/mL) and glucose (0.2%), and were grown at 37° C. until OD600 was 0.8. The cytoplasmic expression of the VHH-CAT-fusion proteins was induced for 2 hours by the addition of 0.2 mM IPTG. At the end of the induction period, bacteria aliquots of 4 µL were plated on LB-agar plates containing IPTG (0.1 mM) and increasing chloramphenicol concentrations ranging from 0 to 500 µg/ml. Bacteria were incubated at 30° C. for 20 hours before quantification of the colony formation. The resistance level was evaluated according to the colony growth rate at the different chloramphenicol concentrations. Several VHH that were giving colonies up to 500 µg/ml were compared to previously characterized intrabodies raised against GFP (nb GFP4) or Lamin (Lam) as well as to a thermostable VHH Re3 and a non intrabody C8. Liquid culture induced as above during 2 hours were diluted by serial dilution and 10 µl were spotted on agar plates containing 250 µg/ml chloramphenicol (Cam) and incubated at 30° C. for 20 hours. Colony were quantified for each dilution and normalized to the higher amount always found with the D10 clone.

Aggregation Assays in Mammalian Cell Expression System
Functional Expression as Intracellular Antibodies in Eukaryote Cells Single domain antibody fragments were subcloned into a mammalian expression vector in order to express it as a fusion with a fluorescent protein and under the control of a CMV promoter. Mammalian cell lines were transfected and fluorescence in the cells was observed 24 h or 48 h after transfection. In comparison to non fused GFP or mCherry, the fluorescence distribution of VHH fused to one of these fluorescent proteins was homogenously spread in transfected cells, showing no obvious aggregates after 48 h of constitutive expression.

Functional Secretion as Fc Fusion

The plasmids are based on the pFUSE-Fc2(IL2ss)™ series from Invivogen (San Diego, USA) that contains the interleukin-2 (IL2) signal sequence and allows the secretion of Fc-Fusion proteins by mammalian cells. Because the hs2dAbs were fused to the hinge domain of IgGs, the Fc domains form di-sulfide bridges and hs2dAb-Fc are expressed as dimmers. They are selectable using Zeocin™ (Zeo) both in prokaryotic and eukaryotic cells. These plasmids were modified by site directed mutagenesis and adaptor insertion (Mould S, et al. BMC Biotechnol. 2009 Feb. 26; 9:14. doi: 10.1186/1472-6750-9-14) to allow the easy one step cassette cloning of recombinant antibodies extracted from a large collection of common recombinant antibody selection and expression plasmids (e.g pHEN, pSEX, pHAL, pCANTAB, pHOG, pOPE, pSTE). Four plasmids were constructed enabling fusion of s2dAb at their C terminus with either human IgG2 (and IgG1) (h), mouse IgG2a (m) or the rabbit IgG (r) Fc domain (Fc regions comprise the CH2 and CH3 domains of the IgG heavy chain and the hinge region).

Four days after transient transfection of CHO or HEK cells with these expression plasmids, secreted antibodies could be available using anti-IgG antibodies directed against the respective Fc species. This allows a large diversity of multiplexing.

Functional Expression in Yeast Two Hybrid System

Antigen coding sequence was cloned in yeast two hybrid bait plasmid lexA (Vojtek and Hollenberg (1995). Methods Enzymol. 255:331-42).

or gal4 (Fromont-Racine, M., Rain, J. C., and Legrain, P. (1997). Nat. Genet. 16: 277-282). DNA binding domain SDAB population to be tested was transferred in yeast two hybrid prey plasmid pGADGH (Bartel, P. L., et al (1993) in Cellular interactions in development: A practical approach. ed. Hartley. D. A. (Oxford University Press, Oxford) pp. 153-179.) by PCR and Gap repair (Orr-Weaver. T. L. and Szostak, J. W. (1983). Proc. Natl. Acad. Sci. USA 80, 4417-4421): DNA prep of pHEN2-3myc plasmid pool (from 1 single clone to 3.109) was prepared. The miniprep DNA was amplify by PCR with oligonucleotide 5p 8328 CCCAC-CAAACCCAAAAAAAGAGATCCTAGAACTAGC-TATGGCCGGACGGGCCAT GGCGGAAGTGCAGCT-GCAGGCTTC (SEQ ID NO:11) and oligonucleotide 3p 8329 ACCGGGCCTCTAGACACTAGCTACTC-GAGGGGCCCCAGTGGCCCTATCTATGCGG CCGCGCTACTCACAGTTAC (SEQ ID NO:12) using pFu polymerase (NEB) using 10 ng of DNA as matrix. The number of tube is depending of the need in DNA quantity and is related to the number of transformant needed. Typically to obtain 1 million yeast transformants, we carried out 8 PCR of 50 µl.

| PCR program | | |
|---|---|---|
| 45 secondes | 94° C. | } ×25 cycles |
| 45 secondes | 94° C. | |
| 45 secondes | 57° C. | |
| 3 minutes | 72° C. | |
| 10 minutes | 72° C. | |
| ∞ | 4° C. | |

PCRs are checked on an agarose gel and concentrated 20 times using ammonium acetate precipitation and resuspended in water.

8 µg of plasmid prey pGADGH digested by NcoI and XhoI and 2 µl of concentrated PCR are transformed in yeast by classical LiAc/PEG transformation. The clones are spread to selective media dropt out minus Tryptophane, Leucine and Histidine. The baits specific clones, identified by this way, are intrabodies from the library that are functional in the yeast cells.

Generation of Synthetic Single Domain Antibody Library and Characterization of Binders Obtained from Said Library We selected a family of highly functional scaffolds, optimized for intracellular expression and high thermostability. This selection was done using fusion proteins between an antibiotic resistance gene and a collection of VHH.

Only bacteria expressing a functional VHH fusion (non aggregating, non degraded) could grow. Expression yield, solubility as GFP fusion in mammalian cells cytoplasm have been further assessed [and compared to selected chromobodies] to select a set of suitable antibodies. The sequences of these antibodies were aligned, and a consensus sequence was defined by the consensus-sdAb framework sequence of the clone D10 see SEQ ID NO:9). In addition to this llama sdAb (IsdAb) we altered the sequence so that it was more similar to human VH, an evolved consensus was thus defined as a synthetic sdAb (hereafter referred as "hs2dAb", see SEQ ID NO:10). We kept the specific hallmarks of VHH at four FR2 positions (37, 44, 45, 47) that are conserved in conventional VH to form the hydrophobic interface with VL and that appeared crucial for intrinsic solubility properties of sdAb (Kastelic D, et al. 2009 J Immunol Methods. October 31; 350(1-2):54-62) (FIG. 1a). We then confirmed that the scaffold was robust and behaving as expected by grafting the CDRs of a known antibody into the IsdAb and s2dAb frameworks. These experiments showed that both IsdAb and hs2dAb allowed efficient display, efficient production in bacteria and in CHO cells, and that it allowed to keep proper reactivity of the grafted CDRs both when expressed in oxidative and in reducing condition. So we decided to select the hs2dAb as a framework to construct our library.

We then introduced a synthetic diversity in the three CDRs without affecting the functionality of the clones. Based on alignment of hundreds of llama sdAb sequences we rationally designed for each position of the CDR1 and CDR2 a set of amino acids that still mimic natural diversity. We voluntarily avoided cysteine residues because thiol groups could later interfere with proper intracellular expression and functionality. We reasoned that lowering the frequency of hydrophobic residues or arginin would avoid aggregation (De Marco A. 2011, Microb Cell Fact. June 9; 10:44 Review) and that lowering as well proline frequency would keep most flexibility in the loops. As serine, threonine and tyrosine are the most frequent residues in CDR loops involved in bonds with the epitope, aspartate and glutamate have been proposed to increase solubility (Lodish H. et al. Molecular Cell Biology. 4th edition. New York: W. H. Freeman, 2000). We voluntarily enriched these five residues at some positions. In contrast we fully randomized some positions of CDR2 as well as each position of CDR3 by introducing all amino acids except cysteine. Nevertheless a diversity in length was also introduced in the CDR3 sequences to enrich binding potential to different epitope shape since nanobodies have been shown to bind both flat surface or cavity (De Genst, E., et al. Proc Natl Acad Sci, (2006) March 21; 103(12):4586-91), or even haptens (Harmsen M M, et al 2007, Appl Microbiol Biotechnol., November; 77(1): 13-22. Review). In order to respect these statistics, to lower the occurrence of too hydrophobic residues or amino-acid promoting aggregation, and in contrast to enrich in polar aminoacid, and to further avoid the occurrence of in frame stop or cysteins and reduce frameshift, the synthesis of the library diversity was achieved by a unique gene synthesis technology that use double strand DNA triplet blocks corresponding to each codon (Van den Brulle J, et al. 2008. Biotechniques. September; 45(3):340-3). All codons were optimized for mammalian cell expression, a SnaBl restriction site was added in FR3 for further CDR3 loop grafting or engineering whereas any other undesired restriction site were avoided in the scaffold.

To generate a large complexity and to reduce the number of empty plasmids, we constructed a novel cloning vector bearing a suicide gene (ccdB) between non compatible cloning sites. Only plasmids were the toxic gene was lost allowed bacteria growth, hence only plasmid bearing a SDAB insert were obtained. CcdB gene is used as a positive selection marker. Most of the test done to detect binding activities, are done using a monovalent selected antibody, means of detection are then based on anti-tag immunostaining. But monovalent tags on monovalent antibodies do not allow strong detection, so we decided to add a triple tag to the novel phagemid that we constructed to increase the power of detection.

To ensure the full diversity of cloned hs2dAbs, the number of theoretical diversity according to the rational design was far above the one of synthesized molecules which was again 4 log above the number of transformed colonies. The most crucial was the very high molecular diversity of hs2dAb synthesized that reached more than $10^{12}$ sequences with a full probability of being unique since it was still above theoretical diversity imposed by the design. The fully synthetic hs2dAb-L1 library was cloned in the pHEN2-3myc vector and up to $3 \cdot 10^9$ colonies were transformed.

The quality and functionality of the hs2dAb-L1 library has been assessed first by sequencing $10^5$ random clones. We then performed screening directed to various kind of Ag with several selection procedures. For the different target tested, we obtained binders with good affinities for EGFP, β-Tubulin, actin, Rho conformational, p53 and Her2. Characterisation of the specificity, affinity and productivity of selected hs2dAb binders is described.

Materials and Methods
Plasmids and Cloning

A synthetic gene (Mister Gene) composed of a 6His-Tag and a triple c-myc Tag was inserted into the pHEN2 phagemid vector (Griffin I. library) between NotI and BamHI sites. The ccdB gene from pENTR™4 vector (Invitrogen) was inserted into the pHEN2 vector between NcoI and NotI sites. For mammalian expression vectors, VHH or hs2dAbs were digested by NcoI and NotI and ligated into the pAOINT or the pmCherry vectors (Clontech).

Cat Assay Filter

The pAO-CAT is a cytoplasmic expression vector that enables to fuse a carboxy-terminal HA-tagged chloramphenicol acetyl transferase (CAT) to the VHH sequences. It has been constructed by cloning a VHH-CAT sequence into the pAOD-Tub1-mGFP vector (Olichon A, et al. 2007. J Biol Chem. December 14; 282(50):36314-20) digested XbaI and KpnI to remove the DsbC-Tub1-mGFP. The VHH-CAT sequence has been obtained by a multi-step PCR strategy. The VHH was amplified using 5' CCTTGATTCTA-GAAATAATTTTGTTTAACTTTAAGAAGGAGATATAC-CATGCTG ATGTCCAGCTGCAGGCGT3 (Fw, SEQ ID NO:13) and 5'CCACCGCTACCGCCGCTGCGG CCGCGTGAGGAGACGGTGACCTOG 03' (Rev, SEQ ID NO: 14). Two sequences of CAT were amplified independently using the pRill plasmid as a template to remove an internal NcoI site. For the N-term, the following primers were used: 5' GCGGCCGCAGCGGCGGTAGCGGTGGC-GAGAAAAAAATCACTGGATATACC 3' (Fw, SEQ ID NO:15) and 5' GCCCATCGTGAAAACGGGGGCG 3' (Rev SEQ ID NO:16).

The C-term was amplified using: 5' CGC-CCCCGTTTTCACGATGGGC 3' (Fw, SEQ ID NO:17) and 5'AGAATAGGTACCAGCGTAATCTGGGACAT-CATAAGGGTAGCCACCCGCCCCGC CCTGCACT-CATCG 3' (Rev SEQ ID NO:18). The three sequences were assembled with a final PCR and the product was digested XbaI and KpnI before being ligated into the vector. Previously selected VHHs from naïve library were subcloned into pAOCAT using the NcoI and NotI restriction sites. Chloramphenicol resistance assay was performed using BL21(DE3) cells transformed with the pAOCAT-VHH fusion constructs. Bacteria were used for inoculating 500 μL of LB containing kanamycin (35 μg/mL) and glucose (0.2%), and were grown at 37° C. until $OD_{600}$ was 0.8. The cytoplasmic expression of the VHH-CAT-fusion proteins was induced for 2 hours by the addition of 0.2 mM IPTG. At the end of the induction period, bacteria aliquots of 4 μL were plated on LB-agar plates containing IPTG (0.1 mM) and increasing chloramphenicol concentrations ranging from 0 to 500 μg/ml. Bacteria were incubated at 30° C. for 20 hours before quantification of the colony formation. The resistance level was evaluated according to the colony growth rate at the different chloramphenicol concentrations. Several VHH that were giving colonies up to 500 μg/ml were compared to previously characterized intrabodies raised against GFP (nb GFP4) or Lamin (Lam) as well as to a thermostable VHH Re3 and a non intrabody C8. Liquid culture induced as above during 2 hours were diluted by serial dilution and to 10 μl were spotted on agar plates containing 250 μg/ml chloramphenicol (Cam) and incubated at 30° C. for 20 hours. Colony were quantified for each dilution and normalized to the higher amount always found with the D10 clone.

The D10 clone was further subcloned into the pHEN6 expression vector, leading to a periplasmic expression higher than 5 mg/L of culture in E coli X11blue strain.

It was subcloned into the pAOint-mGFP and transfected in MRC5, HEK293 or HeLa S3 cells. Transient expression of D10-GFP under the control of a CMV promoter leads to high GFP fluorescence and no aggregation detectable compared to Lam1-GFP or Re3-GFP at 24 h and 48 h.

Library Construction

Gene collections corresponding to the FR and CDR design have been synthesized in vitro (Sloning, GeneArt). 1 μL (10 ng) of the diverse synthesis (corresponding to $1 \cdot 10^{10}$ molecules, hence 10 times the target library diversity) were amplified by PCR in a total volume of 50 μL using 1 μL of Phusion DNA polymerase (New England Biolabs) with an equimolar mixture of the following primers:

```
                                   (SEQ ID NO: 19)
    5'-AACATGCCATCACTCAGATTCTCG-3'

(SEQ ID NO: 20)
    5'-GTTAGTCCATATTCAGTATTATCG-3'
```

PCR protocol consisted of an initial denaturation step at 98° C. for 45 sec followed by 20 cycles of 98° C. for 10 sec, 55° C. for 30 sec and 72° C. for 30 sec, and a final step extension at 72° C. for 10 min. 7×150 μL of PCR were purified on 7 columns of a PCR clean-up kit (Macherey-Nagel). 55 µg of the resulting purified fragment of PCR and 80 µg of the pHEN2-ccdB-3myc phagemid were digested for 2H at 37° C. with NcoI and NotI (NEB) in a total volume of 500 µL. A dephosphorylation step was added for the phagemid with a Calf intestinal alkaline phosphatase (Sigma) 30 min at 37° C. Digestions were purified on gel with respectively 4 and 6 columns of a gel extraction kit (Macherey-Nagel) in a final volume of 80 and 120 µL. Then, purified PCR fragment was ligated into pHEN2-ccdB-3myc, between the PelB leader signal and the pIII gene. 50 µg of phagemid and 19.2 µg of insert were ligated overnight at 16° C. with 10 µL of high concentration T4 DNA ligase (NEB) in a total volume of 400 µL. Ligation was purified on 6 columns (Macherey-Nagel) with a total volume of 150 µL. The ligated DNA material was used to transform electrocompetent *E. coli* TG1 cells (Lucigen). 20 electroporations with 1 µl of ligation were performed according to the manufacturer's instructions (1800V; 10 µF; 600Ω). Each electroporation was resuspended with 1 mL of warm 2×YT, 1% glucose medium and incubated with a shaking agitation for 1H at 37° C. 380 mL of 2×YT, 1% glucose was added to the suspension and plated on 430 2×YT-ampicillin agar dishes (140 mm) overnight at 37° C. Library size was calculated by plating serial dilution aliquots. The colonies were scraped from the plates with liquid 2×TY and library was stored in the presence of 30% of glycerol at −80° C. with 1 mL aliquots at OD=38.4. $3 \cdot 10^9$ individual recombinant clones were obtained.

Library Sequencing:

The heterogeneity of the individual clones from the libraries was checked by sequencing $6 \cdot 10^5$ inserts on ion Torrent chips (Invitrogen).

IonTorrent sequencing library was prepared with the Ion Plus Fragment Library kit for AB Library Builder System (Lite Technologies) following manufacturer's instructions and was controlled on the Agilent 2100 Bioanalyzer (Agilent Technologies) with the High Sensitivity DNA Kit (Agilent Technologies). Sequencing template was prepared by emulsion PCR with the Ion OneTouch 2 system and the Ion PGM Template OT2 400 Kit (Life Technologies). Sequencing was performed on a IonTorrent Personal Genome Machine using the Ion PGM Sequencing 400 Kit and a 314v2 Ion chip (Life Technologies).

Antigens

Human βActin was purchased from Sigma. RhoA GTPase fused to an amino terminal Chitin Binding Domain or a streptactin binding peptide were produced in HEK293 cells. GFP in fusion with a streptavidine binding peptide (SBP) was produced through in vitro translation system (Roche) and used directly for screening without the need for purification (Moutel S, et al. 2009. Biotechnol J. January; 4(1): 38-43). Biotinylated Tubulin was purchased from Cytoskeleton. For p53, the 72 first amino acids of the NP_000537.3 isoform were produced in bacteria with a SNAP Tag and biotinylated in vitro. For Her2, the natural receptor was used as membrane protein target on SKBR3 cells.

Phage Display Selections

Screening for βactin, H1 histone, or FITC were performed by panning in immunotubes as described in Marks J D et al, 1991 J Mol Biol. December 5; 222(3):581-97. Screening for GFP, Tubulin and p53 were performed in native condition as described in Nizak et al. 2003 Science. May 9; 300(5621): 984-7. Screening on Rho was performed in native condition on a tag constitutively active mutant of RhoA expressed in HEK293 cells. Screening for Her2 was performed on surface cells as described in Even-Desrumeaux K, Chames P. 2012 Methods Mol Biol.; 907:225-35.

Enzyme-Linked Immunosorbant Assay (ELISA)

Individual clones were screened as described else-where by monoclonal phage ELISA (Lee, et al; 2007, Nat Protoc. 2(11): 3001-8.

Western-Blot

After boiling in SDS-PAGE loading buffer, the samples were separated on a 12% SDS-PAGE and transferred to nitrocellulose membranes (Whatman GmbH). Membranes were blocked in 3% non-fat milk-PBS with 0.2% Tween 20 for 1 h at room temperature or overnight at 4° C. SDAB were used at 1/100 and added to the membranes with an anti-hisTag antibody at 1/3000 (Sigma) for 90 min. Blots were then washed and incubated 1 h with secondary anti-Mouse HRP labeled antibodies (diluted at 1/10000 in PBS 0.1% Tween 20) (Jakson ImmunoResearch Laboratories). After 5 washes with PBS 0.1% Tween 20, secondary antibodies were then revealed using the SuperSignal chemoluminescent reagent (Pierce) and Hyperfilm ECL (GE HealthCare).

Immunofluorescence

Immunofluorescence screenings were performed on HeLa cells as described before (Nizak et al. 2003. Science. May 9; 300(5621):984-7).

Transient Transfection

Hela Cells cultured on coverslips were transfected according to the CaPO4 procedure with 1 µg DNA per well (24 wells plate) or 10 µg DNA (10 cm2 diameter dish). Cells can be observed from 12 h posttransfection on.

Flow Cytometry

Cell surface staining were performed in phosphate-buffered saline (PBS) supplemented with 1% SFV. 100 µl of supernatant (80 µl phages+20 µl PBS/milk 1%) were incubated on $1.10^5$ cells for 1 h on ice. Phage binding was detected by a 1:300 dilution of anti-M13 Ab (GE healthcare) for 1 h on ice followed by a 1:1000 dilution of PE-conjugated anti-Mouse Ab (BD Pharmingen.) for 45 min. Samples were analyzed by flow cytometry on a FACSCalibur using CellQuest Pro software (BD Biosciences, San Jose, Calif.).

Affinity Measurement

The binding affinity of the hs2dAb antibodies selected from the library and specific for GFP and ErBB2 were performed at 25° C. using a ProteOn XPR36 (BioRad) and a Biacore T200 (GE Healthcare), respectively, and fitted with a 1:1 Langmuir interaction model. The ligand GFP (24 kDa) was diluted to 1.6 µM in sodium acetate buffer (pH 5.0) and immobilized by amine-coupling on a GLC chip (Bio-Rad) at 730 RU. 100 µL of monovalent single-domain antibodies (14 kDa) were used as an analyte and injected at 100 µL/min at concentrations between 1000 and 3 µM (60 second injection, 600 second dissociation). The complete kinetic set was collected in a single run (one-shot) and, therefore, there was no need for surface regeneration. ErbB2 ectodomain-Fc (96 kDa) was diluted to 400 µg/mL in sodium acetate buffer (pH 5.0) and immobilized by amine-coupling on a CM5 chip (GE Healthcare) at 991 RU. Monovalent single-domain antibodies (14 kDa) were diluted in HBS-EP+ buffer and injected as analytes at 30 µL/min at concentrations between 300 and 3 µM using the single-cycle modality (120 second injection, 120 second intermediate dissociation, 600 second final dissociation). The kinetics were collected in a unique sequence of injections and surface regeneration (10 mM glycine HCl, pH 2.5, for 30 s at 30 µL/min) took place only between two successive series.

Results
Library Design

In the view of making a large single domain antibody library enriched in highly stable and functional antibody fragments, we aimed at identifying a single VHH scaffold. We previously selected several hundreds of clones from immune or naïve llama VHH libraries (Monegal A, et al. 2012 Dev Comp Immunol. January; 36(1):150-6). We screened a set of highly expressed clones using a chloramphenicol filter assay that discriminate highly stable clone from the one prone to aggregation or unfolding in bacteria cytoplasm (Olichon). We used the pAO-CAT cytoplasmic expression vector that enables to fuse a carboxy-terminal HA-tagged chloramphenicol acetyl transferase (CAT) to the VHH sequences. By comparison with published thermostable VHH (Olichon A. et al BMC Biotechnol. 2007 Jan. 26:7:7) or intrabodies (Rothbauer U, et al Nat Methods. 2006 November; 3(11):887-9), one scaffold, clone D10, was showing higher chloramphenicol resistance (FIG. 1a). The D10 VHH was further fitting all our criteria of solubility, thermostability and no aggregation while expressed as an intrabody in mammalian cells, in the absence of any known antigen recognition. We then assessed if partial humanization (Vincke C, et al. J Biol Chem. 2009 Jan. 30; 284(5): 3273-84) of the scaffold would affect its intrinsic properties by targeting seven residues that are found in human VH3. The four VHH-specific amino acids hallmarks in the framework-2 region (positions 42, 49, 50, and 52) that appeared crucial for intrinsic solubility properties (FIG. 1c) were kept untouched.

To test whether this scaffold may be suitable for antigen binding and used as a general scaffold for library construction, we grafted loops of the lam1 VHH specific of laminB protein (Rothbauer U, et al. Nat Methods. 2006 November; 3(11):887-9). FIG. 2a shows that both scaffolds (IsdAbB and hs2dAb) do not perturb the display of the recombinant antibody on phages, here labelled with an anti-pIII antibody. The yield of production from culture supernatants either from E. coli or from mammalian CHO cells (Moutel S, et al BMC Biotechnol. 2009 Feb. 26; 9:14. doi: 10.1186/1472-6750-9-14) were also high and comparable for both scaffolds, (see FIG. 2b). The grafted synthetic antibodies were then used to stain HeLa cells by indirect immunofluorescence. Both grafted single domain antibodies produced the expected staining indicating that they efficiently stained endogenous Lamin B (FIG. 2c). The two synthetic antibodies were then fused to EGFP and used as intrabodies. After transient transfection of HeLa cells, both fluorescent antibodies were soluble and labelled their intracellular target (FIG. 2d), as was observed when using the original lam1 VHH antibody (Rothbauer U, et al 2006). Both scaffold, Lama and Humanized D10, grafted with lam1 CDR loops thus retained the binding property of the parental VHH. <.

Altogether, these experiments indicated that the synthetic scaffold of humanized D10 (herein called Synthetic Single Domain Antibody or hs2dAb) is an efficient and robust framework to display CDR loops.

Library Construction

We introduced a synthetic diversity in the three CDRs by rationally designing a set of amino acids that still mimic natural diversity for each position of the CDR1 and CDR2 (based on statistical analysis of CDRs found in published VHH binders). The amino acids residues of the synthetic CDR1 and CDR2 have been determined by the following rules:
at CDR1 position 1: Y, R, S, T, F, G, A, or D;
at CDR1 position 2: Y, S, T, F, G, T, or T;
at CDR1 position 3: Y, S, S, S F, or W;
at CDR1 position 4: Y, R, S, T, F, G, A, W, D, E, K or N;
at CDR1 position 5: S, T, F, G, A, W, D, E, N, I, H, R, Q, or L;
at CDR1 position 6: S, T, Y, D, or E;
at CDR1 position 7: S, T, G, A, D, E, N, I, or V;
at CDR2 position 1: R, S, F, G, A, W, D, E, or Y.
at CDR2 position 2: S, T, F, G, A, W, D, E, N, H, R, Q, L or Y;
at CDR2 position 3: S, T, F, G, A, W, D, E, N, H, Q, P;
at CDR2 position 4: O, S, T, N, or D;
at CDR2 position 5: S, T, F, G, A, Y, D, E, N, I, H, R, Q, L, P, V, W, K or M;
at CDR2 position 6: S, T, F, G, A, Y, D, E, N, I, H, R, Q, L, P, V, W, or K;
at CDR2 position 7: S, T, F, G, A, Y, D, E, N, I, H, R, Q, L, P, or V;

The CDR3 amino acid sequence comprises 9, 12, 15 or and 18 amino acids selected among one or more of the following amino acids: S, T, F, G, A, Y, D, E, N, I, H, R, Q, L, P, V, W, K, M.

Synthetic DNA was amplified using a low number of PCR cycles to prevent the addition of PCR-based mutations. We started the construction with $2 \cdot 10^{11}$ different molecules. We cloned the synthetic library in the pHEN2 phagemide vector modified by adding 2 supplemental myc-tags with a synthetic gene (Proteogenix) between the recombinant Ab and the pIII gene. These additional myc-tags allow better revelation of monovalent Ab (data not shown). For the cloning we added also a suicide gene (ccdB) between NcoI and NotI that allows a positive selection of clones that have inserted the library. A large amount of phagemid and insert were used to obtain a lot of material to electroporate E. coli TG1 cells. 20 electroporations were performed to produce the hs2dAb-L1 library. Transformed bacteria were plated on 430 large agar plates (140 mm). The library size was calculated by plating serial dilution aliquots and was estimated to be of $3 \cdot 10^9$ individual clones.

Library Sequencing:

We first evaluated the functional diversity by sequencing 315 random clones with Sanger sequencing. 9 sequences were found either with stop codon or with the missing of one base, one sequence missed all the CDR1, one other missed CDR1, FR1 and CDR2, and two last sequences were found empty. Thus, only a very low number (4.1%) of defective clones were obtained. Which suggest that the vast majority of the 3 $10^9$ clones will express a recombinant hs2dAb.

The heterogeneity of the individual clones from the libraries was further checked by sequencing $5.6 \cdot 10^5$ inserts on ion Torrent chips (Life Technologies). The distribution of length sequences for the 4 sizes of CDR3 was homogenous. The diversity and positional amino acids frequency were in agreement with our design for all CDRs (data not shown). 3 redundant clones were found but this observation may be linked to the PCR amplification done during the Next-Generation Sequencing procedure.

Library Screening

The hs2dAb-L1 library was screened by phage display using standard methods (Hoogenboom H R. et al. 1998 June; 4(1):1-20) against a set of different antigens reported in Table 1. To validate the use of hs2dAb-L1 in various screening approaches, we either carried out selection on beads (which offers a large capacity of antigen presentation and keep the antigen conformation closer to native protein), either panning on immunotubes (referenced as standard method) or on natural antigen presented naturally on the surface of mammalian cells (as often done when applying in vitro selection to therapeutic questions).

A first screening was performed in native condition (Nizak, 2005, see supra) using biotinylated tubulin (Cytoskeleton) as a target. After two rounds of selection, 40 clones were screened at random by immunofluorescence on HeLa cells fixed with methanol. 3 recombinant Ab stained the endogenous tubulin (FIG. 3A). These 3 clones were also usable in Western-Blotting of human protein samples (FIG. 3A). A second screening was performed against endogenous Her2 receptor expressed at the surface of SKBR3 cells. A pre-adsorption of the phages was done at each of the 3 rounds on Her2 negative MC10A cells to counter select non-SKBR3 specific antibodies. Using a FACS assay, 17 specific anti-SKBR3 binders were found out of 84 analysed that could be grouped in 17 non-redundant sequences. Analysis by ELISA, using Her2 ectodomain-Fc (96 kDa) as a target, showed that 12 of them were directed against HER2 (FIG. 3B). Immunofluorescence confirmed that the antibodies decorated the SKBR3 plasma membrane (data not shown). A third screening was performed directed against the tumor suppressor p53 protein. The 72 first amino acids of the NP_000537.3 isoform were produced in bacteria fused to a SNAP Tag, biotinylated in vitro and used as a target on beads. After 3 rounds of selection, 12 clones out of 80 were found positive in phage ELISA (data not shown), 6 clearly labelled endogenous p53 in immunofluorence on A431 cells (data not shown) while 2 were usable as intrabodies on HeLa cells (see FIG. 4). As expected, no staining was observed on U2OS cells which are p53−/−. A fourth screening was performed to obtain conformational binder of Rho-GTP protein. After four rounds of competitive selection (see materials and methods), 80 unique clones were tested in ELISA on using recombinant GST-RhoA proteins loaded with GDP of the non-hydrolysable analogue GTPγS. 24 antibodies gave a stronger signal against GTPγS-RhoA than against GDP-Rho, indicating conformational binding. One of the antibodies, the H12 clone, dominated the screen and was the only clone obtained upon an additional 5th round of selection. We tested these conformational binders in immunofluorescence on HeLa cells expressing SF-GFP (superfolder GFP) fusion of RhoA negative mutant N19 (GDP-bound) or the constitutively active mutant L63 (GTP-bound). None of the clones stained cells expressing the N19 negative mutant while 8 of them efficiently stained cells overexpressing the active form of RhoA. We further characterized the clone H12 and tested its ability to pull down endogenous RhoA from HeLa cell extracts incubated with GTPγS or GDP. We showed that purified H12 antibody was an effective conformational biosensor of Rho activity usable in ELISA, immunofluorescence and in vitro pull down experiments. We further observed that it was more effective than the conventional RBD activity assay were the Rho Binding Domain of an effector protein is used as a biosensor. (FIG. 3C, IF and ELISA Data not shown). A fifth screening in native conditions was performed using the GFP protein as a target. Thirty seven non redundant clones out of 80 analysed were positive in phage ELISA (data not shown). Ten of them detected GFP-myr-palm, by immunofluorescence (data not shown). Importantly, we observed that 4 of these antibodies were usable as intrabodies against recombinant GFP expressed in Hela cells (FIG. 4). A last screen was performed using to immunotubes coated with native commercial bActin (Sigma). This last screening allowed the selection of 16/S0 unique binders as observed by phage ELISA (data not shown), Seven of them clearly decorated endogenous actin stress fibers in HeLa cells (data not shown) and 4 were usable for Western-Blotting experiments (data not shown).

TABLE 1

Summary of screening Positive clones

| Antigen | Phage ELISA | IF/FACS | Intrabody | Rounds of punning |
|---------|-------------|---------|-----------|-------------------|
| GFP | 37 | 10/ | 4/10 | 2 |
| mCherry | ND | 6/ | 2/6 | 3 |
| Tubulin | ND | 3/ | 0/3 | 2 |
| Actin | 11 | 9/ | 1/7 | 3 |
| p53 | 12 | 6/ | 2/6 | 2 |
| RhoA-GTP | 24 | 8/ | 3/8 | 4 |
| Her2 | 15 | 5/10 | ND | 3 |

Affinity Measurement

Affinity of single domain antibodies against GFP, Her2 and p53 were measured using a ProteOn XPR36 (BioRad) or a Biacore T200 (GE Healthcare). Affinities were estimated to be in the nanomolar range: $3.06 \cdot 10^{-8}$ M for anti-GFP, $1.94 \cdot 10^{-8}$ M for anti-Her2 and $3.25 \cdot 10^{-8}$ M for anti-p53, demonstrating that high affinity binders could be obtained from our hs2dAb-L1 library of synthetic, non immune, single domain Ab (FIG. 5).

Inhibitory Intrabodies

Identification of blocking antibodies is a challenging task. However, it is possible to functionalize non-blocking intrabodies to inhibit their target function. One approach relies on the ubiquitinylation and degradation of the recognized target as described by Caussinus et al. 2011 (Caussinus et al. 2011, Nat. Struct. Mol. Biol. 19, 117-121). This approach is based on the fusion of intrabodies to an F-box domain which allows interaction with Skip1, a member of the SCF complex, an E3 ubiquitin ligase of the complex E1/E2/E3 ubiquitinylation machinery, that target proteins to proteasome-dependent cellular degradation. This approach was initially developed to target several GFP fusion proteins in Drosophila using a single anti GFP intrabody, named GFP4, which is a robust high affinity GFP llama intrabody originally isolated from an immune library (Rothbauer, U. et al. Nat. Methods 3, 887-889). To get insight into the relative functionality of hs2dAb for such a protein knockdown approach, we fused several of our anti GFP hs2dAb at their amino terminus to the Fbox domain and compared their efficacy with the efficacy of the Fbox-GFP4 antibody. To detect cells expressing Fbox-intrabody fusion proteins (F-Ib), we constructed a bicistronic vector driving the co-expression of F-Ib together with a mitochondria-targeted mCherry (Mito-mCherry). We expressed the F-Ib antibodies in a HeLa clone stably expressing GFP fused to histone H2B (Silljé, H. H. W., Nagel. S., Körner, R. & Nigg, E. A., 2006, Curr. Biol. CB 16, 731-742) and looked for GFP-H2B depletion. As expected, F-GFP4, also known as degradFP, induced a strong reduction of H2B-GFP expression as analyzed by western blot (data not shown). Accordingly, a strong reduction in nuclear fluorescence intensity was observed in cells expressing F-GFP4. No effect was observed % when expressing either GFP4 alone or a GFP4 fused to a truncated, nonfunctional, Fbox domain. When we tested anti-GFP clones selected from our novel library, we observed that several hs2dAb that were found to be efficient when used as fluorescent intrabodies failed to degrade H2B-GFP when expressed as F-Ib. This highlights the fact that not all intrabodies can efficiently be functionalized with the F-box. However, one hs2dAb anti-GFP induced a complete disappearance of nuclear H2B-GFP signal when expressed as F-Ib. FACS analysis showed a fluorescence intensity decreased as much as 70%. As expected, this effect was reversed in the presence of proteasome inhibitor treatment.

Altogether, these experiments show that the hs2dAb scaffold enables the frequent selection of antibodies that can be expressed in the mammalian cell cytoplasm to be used as fluorescent intrabodies or inhibitory intrabodies.

| | Useful Sequences for practicing the invention | |
|---|---|---|
| SEQ ID NO: | Description | Sequence |
| 1 | single domain antibody FR1 | VQLQASGGGFVQPGGSLALSCAASG |
| 2 | single domain antibody FR2 | MGWFRQAPGKEREFVSAIS |
| 3 | single domain antibody FR3 | YYADSVKGRFTISRDNSKNTVYLQMNSLRAEDTATYYCA |
| 4 | single domain antibody FR4 | YWGQGTQVTVSS |
| 5 | coding nucleic acid sequence of SEQ ID NO: 1 | ATGGCGGAAGTGCAGCTGCAGGCGAGCGGCGGCG GCTTTGTGC AGCCGGGCGGCAGCCTGCGTCTGAGCTGCG CGGCGAGCGGC |
| 6 | coding nucleic acid sequence of SEQ ID NO: 2 | ATGGGCTGGTTTCGTCAGGCGCCGGGCAAAGAACG TGAATTTG TGAGCGCGATTAGC |
| 7 | coding nucleic acid sequence of SEQ ID NO: 3 | TATTATGCGGATAGCGTGAAAGGCCGTTTTACCATT AGCCGTGATAACAGCAAAAA CACCGTGTATCTGCAGATGAACAGCCTGCGTGCGG AAGATACCGCTACGTATTATTGCGCG |
| 8 | coding nucleic acid sequence of SEQ ID NO: 4 | TATTGGGGCCAGGGCACCCAGGTGACCGTGAGCAG CGCGGCCGCA |
| 9 | Non humanized sequence of clone D10 | VQLQESGG GFVQAGGSLR LSCAASGFTF SSYAMGWFRQ APGKEREFVA AISDSSGNHAYVADSVKG RFTISRDNAK NTVYLQMNSL KPEDTATYYC ARSDAAGNPS GYWGQGTQVTVSS |
| 10 | Humanized sequence of clone D10 | VQLQASGG GFVQPGGSLR LSCAASGFTF SSYAMGWFRQ APGKEREFVS AISDSSGNHAYVADSVKG RYTISRDNSK NTVYLQMNSL RAEDTATYYC ARSDAAGNPS GYWGQGTQVTVSS |
| 11 | oligonucleotide 5p 8328 | CCCACCAAACCCAAAAAAAGAGATCCTAGAACTA GCTATGGCCGGACGGGCCATGGCGGAAGTGCAGCT GCAGGCTTC |
| 12 | oligonucleotide 3p 8329 | ACCGGGCCTCTAGACACTAGCTACTCGAGGGGCCC CAGTGGCCCTATCTATGCGGCCGCGCTACTCACAG TTAC |
| 13 | VHH Fw primer | CCTTGATTCTAGAAATAATTTTGTTTAACTTTAAGA A GGAGATATACCATGCTGATGTCCAGCTGCAGGCGT |
| 14 | VHH Rev primer | CCACCGCTACCGCCGCTGCGG CCGCGTGAGGAGAC GGTGACCTGG G |
| 15 | Fw N-term | GCGGCCGCAGCGGCGGTAGCGGTGGCGAGAAAAA AATCACTGGATATACC |
| 16 | Rev N-term | GCCCATCGTGAAAACGGGGGCG |
| 17 | Fw C-term | CGCCCCCGTTTTCACGATGGGC |
| 18 | Rev C-term | AGAATAGGTACCAGCGTAATCTGGGACATC ATAAGGGTAGCCACCCGCCCCGCCCTGCACTCATC G |

| Useful Sequences for practicing the invention | | |
|---|---|---|
| SEQ ID NO: | Description | Sequence |
| 19 | Primer library | AACATGCCATCACTCAGATTCTCG |
| 20 | Primer library | GTTAGTCCATATTCAGTATTATCG |

The invention claimed is:

1. An antigen-binding protein, comprising a synthetic single domain antibody of the following formula: FR1-CDR1-FR2-CDR2-FR3-CDR3-FR4, wherein said framework regions consist of FR1 of SEQ ID NO:1, FR2 of SEQ ID NO:2, FR3 of SEQ ID NO: 3 and FR4 of SEQ ID NO:4.

2. The antigen-binding protein of claim 1, wherein said synthetic single domain antibody has one or more of the following functional properties:
   i. it can be expressed as soluble single domain antibody in *E. coli* periplasm,
   ii. it can be expressed as soluble intrabodies in *E. coli* cytosol,
   iii. it is stable in reducing environment in chloramphenicol acetyl transferase fusion assay,
   iv. it does not aggregate when expressed in mammalian cell lines as fluorescent protein fusions.

3. The antigen-binding protein of claim 1, wherein the amino acid residues of the synthetic CDR1 and CDR2 are:
   at CDR1 position 1: Y, R, S, T, F, G, A, or D;
   at CDR1 position 2: Y, S, T, F, G, T, or T;
   at CDR1 position 3: Y, S, F, or W;
   at CDR1 position 4: Y, R, S, T, F, G, A, W, D, E, K or N;
   at CDR1 position 5: S, T, F, G, A, W, D, E, N, I, H, R, Q, or L;
   at CDR1 position 6: S, T, Y, D, or E;
   at CDR1 position 7: S, T, G, A, D, E, N, I, or V;
   at CDR2 position 1: R, S, F, G, A, W, D, E, or Y;
   at CDR2 position 2: S, T, F, G, A, W, D, E, N, H, R, Q, L or Y;
   at CDR2 position 3: S, T, F, G, A, W, D, E, N, H, Q, P;
   at CDR2 position 4: G, S, T, N, or D;
   at CDR2 position 5: S, T, F, G, A, Y, D, E, N, I, H, R, Q, L, P, V, W, K or M;
   at CDR2 position 6: S, T, F, G, A, Y, D, E, N, I, H, R, Q, L, P, V, W, or K;
   at CDR2 position 7: S, T, F, G, A, Y, D, E, N, I, H, R, Q, L, P, or V;
   and wherein CDR3 amino acid sequence comprises between 9 and 18 amino acids selected among one or more of the following amino acids: S, T, F, G, A, Y, D, E, N, I, H, R, Q, L, P, V, W, K, M.

4. The antigen-binding protein of claim 1, further comprising a F-box domain for targeting a protein to the proteasome.

* * * * *